| (12) | United States Patent | (10) Patent No.: | US 8,702,423 B2 |
|---|---|---|---|
| | Better et al. | (45) Date of Patent: | Apr. 22, 2014 |

(54) CORTICAL DRILLING

(75) Inventors: Hadar Better, Tel Aviv (IL); Gideon Fostick, Givat Shmuel (IL); Ilan Uchitel, Kefar Saba (IL); Yossi Gross, Moshav Mazor (IL)

(73) Assignee: Maxillent Ltd., Herzliya (IL)

( * ) Notice: Subject to any disclaimer, the term of this patent is extended or adjusted under 35 U.S.C. 154(b) by 243 days.

(21) Appl. No.: 13/314,740

(22) Filed: Dec. 8, 2011

(65) Prior Publication Data

US 2013/0150857 A1 Jun. 13, 2013

(51) Int. Cl.
*A61C 8/00* (2006.01)
*A61C 3/02* (2006.01)

(52) U.S. Cl.
USPC .............. 433/172; 433/173; 433/165; 433/76

(58) Field of Classification Search
USPC .............. 433/72–76, 165–166, 172–176, 215, 433/224, 102; 606/80, 96; 128/898
See application file for complete search history.

(56) References Cited

U.S. PATENT DOCUMENTS

| 2,347,567 | A | 4/1944 | Kresse |
|---|---|---|---|
| 2,436,623 | A | 2/1948 | Zile |
| 3,659,881 | A | 5/1972 | Tinsley et al. |
| 4,021,921 | A | 5/1977 | Detaille |
| 4,112,944 | A | 9/1978 | Williams |
| 4,412,825 | A | 11/1983 | Tokarz |
| 4,416,629 | A | 11/1983 | Mozsary et al. |
| 4,431,416 | A | 2/1984 | Niznick |
| 4,473,353 | A | 9/1984 | Greggs |
| 4,523,910 | A | 6/1985 | Makovich |
| 4,854,872 | A | 8/1989 | Detsch |
| 4,960,381 | A | 10/1990 | Niznick |
| 5,022,857 | A | 6/1991 | Matsutani et al. |
| 5,047,030 | A | 9/1991 | Draenert |
| 5,049,125 | A | 9/1991 | Accaries et al. |
| 5,078,605 | A | 1/1992 | Sutter et al. |
| 5,188,488 | A | 2/1993 | Nakayama et al. |
| 5,261,818 | A | 11/1993 | Shaw |
| 5,284,688 | A | 2/1994 | Hiatt |
| 5,291,914 | A | 3/1994 | Bares et al. |
| 5,312,255 | A | 5/1994 | Bauer |
| 5,366,374 | A | 11/1994 | Vlassis |
| 5,456,601 | A | 10/1995 | Sendax |
| 5,481,260 | A | 1/1996 | Buckler et al. |
| 5,575,650 | A | 11/1996 | Niznick et al. |

(Continued)

FOREIGN PATENT DOCUMENTS

| EP | 1174094 A1 | 1/2002 |
|---|---|---|
| WO | WO2007007331 A1 | 1/2007 |

(Continued)

OTHER PUBLICATIONS

An Office Action dated Mar. 15, 2013, which issued during the prosecution of U.S. Appl. No. 13/196,632.

(Continued)

*Primary Examiner* — Yogesh Patel
(74) *Attorney, Agent, or Firm* — Fish & Richardson P.C.

(57) ABSTRACT

A method is provided that includes advancing a drill having a distal end through an occlusal cortex into trabecular bone of an alveolar ridge, and ceasing the advancing of the drill when the distal end of the drill reaches an occlusal surface of a superior cortex of the alveolar ridge. Other embodiments are also described.

13 Claims, 17 Drawing Sheets

(56) References Cited

U.S. PATENT DOCUMENTS

| | | | |
|---|---|---|---|
| 5,685,716 | A | 11/1997 | Linkow |
| 5,711,315 | A | 1/1998 | Jerusalmy |
| 5,759,036 | A | 6/1998 | Hinds |
| 5,782,918 | A | 7/1998 | Klardie et al. |
| 5,795,160 | A | 8/1998 | Hahn et al. |
| 5,829,977 | A | 11/1998 | Rogers et al. |
| 5,839,899 | A | 11/1998 | Robinson |
| 5,868,572 | A | 2/1999 | Lazzara et al. |
| 5,879,161 | A | 3/1999 | Lazzara |
| 5,915,967 | A | 6/1999 | Clokie |
| 5,967,777 | A | 10/1999 | Klein et al. |
| 5,989,025 | A | 11/1999 | Conley |
| 6,068,479 | A | 5/2000 | Kwan |
| 6,159,161 | A | 12/2000 | Hodosh |
| 6,200,289 | B1 | 3/2001 | Hochman et al. |
| 6,220,860 | B1 | 4/2001 | Hansson |
| 6,270,346 | B1 | 8/2001 | Grabenhofer et al. |
| 6,273,720 | B1 | 8/2001 | Spalten |
| 6,758,673 | B2 | 7/2004 | Fromovich et al. |
| 6,939,135 | B2 | 9/2005 | Sapian |
| 7,100,476 | B1 | 9/2006 | Feit |
| 7,217,130 | B2 | 5/2007 | Giorno |
| 7,297,102 | B2 | 11/2007 | Smith et al. |
| 7,300,282 | B2 | 11/2007 | Sapian |
| 7,364,430 | B2 * | 4/2008 | Kitamura et al. ............. 433/173 |
| 7,396,232 | B2 | 7/2008 | Fromovich et al. |
| 7,510,397 | B2 | 3/2009 | Hochman |
| 7,934,929 | B2 | 5/2011 | Better et al. |
| 8,029,284 | B2 | 10/2011 | Better et al. |
| 8,388,343 | B2 | 3/2013 | Better et al. |
| 2003/0105469 | A1 | 6/2003 | Karmon |
| 2003/0175656 | A1 | 9/2003 | Livne et al. |
| 2003/0228556 | A1 | 12/2003 | Giorno |
| 2003/0232308 | A1 | 12/2003 | Simmons |
| 2006/0020326 | A9 | 1/2006 | Bolduc et al. |
| 2006/0084034 | A1 | 4/2006 | Hochman |
| 2006/0172255 | A1 | 8/2006 | Hochman et al. |
| 2006/0210949 | A1 * | 9/2006 | Stoop ............................ 433/165 |
| 2007/0055257 | A1 | 3/2007 | Vaccaro et al. |
| 2007/0162024 | A1 | 7/2007 | Siemonsmeier |
| 2007/0238068 | A1 | 10/2007 | Comfortes |
| 2008/0108011 | A1 | 5/2008 | Nahlieli |
| 2008/0161934 | A1 * | 7/2008 | Yamada ...................... 623/17.17 |
| 2008/0182225 | A1 | 7/2008 | Gordils |
| 2008/0213729 | A1 | 9/2008 | Hochman |
| 2008/0215010 | A1 | 9/2008 | Silver et al. |
| 2008/0293010 | A1 * | 11/2008 | Song ............................ 433/165 |
| 2008/0319466 | A1 | 12/2008 | Eder |
| 2009/0136898 | A1 | 5/2009 | Kim |
| 2009/0142731 | A1 * | 6/2009 | Kim ............................. 433/165 |
| 2009/0186317 | A1 | 7/2009 | Allon |
| 2009/0239200 | A1 * | 9/2009 | Brajnovic et al. ............. 433/215 |
| 2009/0326537 | A1 | 12/2009 | Anderson |
| 2010/0047733 | A1 | 2/2010 | Nahlieli |
| 2010/0081111 | A1 | 4/2010 | Better et al. |
| 2010/0081112 | A1 | 4/2010 | Better et al. |
| 2010/0196841 | A1 | 8/2010 | Nahlieli et al. |
| 2010/0255446 | A1 | 10/2010 | Better et al. |
| 2010/0266984 | A1 * | 10/2010 | Jung ............................ 433/166 |
| 2010/0324561 | A1 | 12/2010 | Watzek et al. |
| 2011/0008746 | A1 * | 1/2011 | Kim ................................ 433/25 |
| 2011/0165536 | A1 | 7/2011 | Better et al. |
| 2011/0212415 | A1 | 9/2011 | Better et al. |
| 2012/0094254 | A1 | 4/2012 | Uchitel et al. |

FOREIGN PATENT DOCUMENTS

| | | | |
|---|---|---|---|
| WO | W02007114553 | A1 | 10/2007 |
| WO | W02007080595 | A3 | 4/2009 |
| WO | W02010035270 | A3 | 5/2010 |
| WO | W02010146573 | A1 | 12/2010 |

OTHER PUBLICATIONS

An Office Action dated Mar. 19, 2013, which issued during the prosecution of U.S. Appl. No. 13/409,631.

An Office Action dated Mar. 29, 2013, which issued during the prosecution of U.S. Appl. No. 13/228,564.

An Office Action dated Oct. 16, 2012, which issued during the prosecution of U.S. Appl. No. 12/661,795.

An Office Action dated Jun. 20, 2013, which issued during the prosecution of U.S. Appl. No. 13/196,632.

An Office Action dated Jun. 26, 2013, which issued during the prosecution of U.S. Appl. No. 13/409,631.

An Office Action dated Jun. 26, 2013, which issued during the prosecution of U.S. Appl. No. 13/760,206.

An Office Action dated Jun. 24, 2013, which issued during the prosecution of U.S. Appl. No. 13/314,818.

Bränemark System® product description, Nobel BiocareTM AB (Zurich, Switzerland) (downloaded from http://www1.nobelbiocare.com/en/implants-and-abutments/products/parallelled-walled-implants/Branemark-system.aspx on Mar. 12, 2010).

Chen L et al., "An 8-year retrospective study: 1,100 patients receiving 1,557 implants using the minimally invasive hydraulic sinus condensing technique," J Periodontol 76:482-491 (2005).

Flanagan D, "Important arterial supply of the mandible, control of an arterial hemorrhage, and report of a hemorrhagic incident," J Oral Implantol 29(4):165-73 (2003).

Muronoi M et al., "Simplified procedure for augmentation of the sinus floor using a haemostatic nasal balloon," British Journal of Oral & Maxillofacial Surgery 41(2):120-121 (2003).

Lee S et al., "Crestal Sinus Lift: A Minimally Invasive and Systematic Approach to Sinus Grafting," The Journal of Implant & Advanced Clinical Dentistry 1(1) (Mar. 2009).

NobelActiveTM External Connection product catalog, Nobel BiocareTM AB (Zurich, Switzerland) (2007).

Pjetursson et al., "Maxillary sinus floor elevation using the (transalveolar) osteotome technique with or without grafting material. Part I: implant survival and patients' perception," Clin Oral Impl Res 20:667-676 (2009).

Riley ET et al., "The Episure syringe: a novel loss of resistance syringe for locating the epidural space," Anesth Analg. 105(4):1164-6 (Oct. 2007).

SinCrest brochure, Meta Advanced Medical Technology C.G.M. S.p.A. (Reggio Emilia, Italy) (downloaded Sep. 1, 2008).

Sinus Lift Kit brochure, Cowellmedi USA Inc. (Buena Park, CA, USA) received on Mar. 15, 2011.

Sotirakis E, "A different method for elevation of the floor of the maxillary sinus: Experimental study and reference to some cases," Mediterranean Dental Implant Congress (Athens, Greece), Scientific Programme MDIC (2004). Abstract only.

Vercellotti T, "Piezoelectric surgery in implantology: a case report—a new piezoelectric ridge expansion technique," Int J Periodontics Restorative Dent 20(4):358-65 (2000).

Vercellotti T et al., "The Piezoelectric Bony Window Osteotomy and Sinus Membrane Elevation: Introduction of a New Technique for Simplification of the Sinus Augmentation Procedure," Int J Periodontics Restorative Dent 21(6):561-7 (2001).

Zimmer ERATM Mini Dental Implant System Usage Guide, Zimmer Dental (Carlsbad, CA) (Dec. 2009).

Zimmer Tapered Screw-Vent® Implant System product catalog, Zimmer Dental Inc. (Carlsbad, CA, USA) (2008).

Zimmer Tapered Screw-Vent® Implant System Product Catalog, Zimmer Dental Inc. (Carlsbad, CA, USA) (Mar. 2009).

Zimmer Spline® Implant System Product Catalog, Zimmer Dental Inc. (Carlsbad, CA, USA) (Feb. 2007).

Zimmer SwissPlus® Implant System Product Catalog, Zimmer Dental Inc. (Carlsbad, CA, USA) (Jan. 2007).

Zimmer ERATM Mini Dental Implant System Product Catalog, Zimmer Dental Inc. (Carlsbad, CA, USA) (Feb. 2010).

Fritz ME et al. The use of Guided Bone Regeneration to fill Large Mandibular Defects in Monkeys, A Pilot Study, JOMI, pp. 644-652, Jun 1994.

Bui DX, Guided Bone Regeneration downloaded from http://www.drbui.com/artgbr.html Dec. 19 2011.

Kawana (Kawana) et al. Acquisition of Bone Structure in Drilling process using Cutting force Estimation, pp. 393-398, Nov. 2010, Yokohama, Japan.

(56) References Cited

OTHER PUBLICATIONS

An Office Action dated Jan. 6, 2011, which issued during the prosecution of U.S. Appl. No. 12/240,353.
An Office Action dated Oct. 1, 2010, which issued during the prosecution of U.S. Appl. No. 12/240,353.
An Office Action dated Apr. 11, 2011, which issued during the prosecution of U.S. Appl. No. 12/485,199.
An Office Action dated Jun. 27, 2011, which issued during the prosecution of U.S. Appl. No. 12/485,199.
An Office Action dated Dec. 27, 2011, which issued during the prosecution of U.S. Appl. No. 12/661,795.
U.S. Appl. No. 60/619,542, filed Oct. 15, 2004.
An International Search Report dated Mar. 23, 2010, which issued during the prosecution of Applicant's PCT/IL2009/000931.
An International Preliminary Report on Patentability dated Mar. 29, 2011, which issued during the prosecution of Applicant's PCT/IL2009/000931.
An International Search Report dated Jul. 15, 2010, which issued during the prosecution of Applicant's PCT/IL2010/000252.
An International Preliminary Report on Patentability dated Dec. 16, 2011, which issued during the prosecution of Applicant's PCT/IL2010/000252.

* cited by examiner

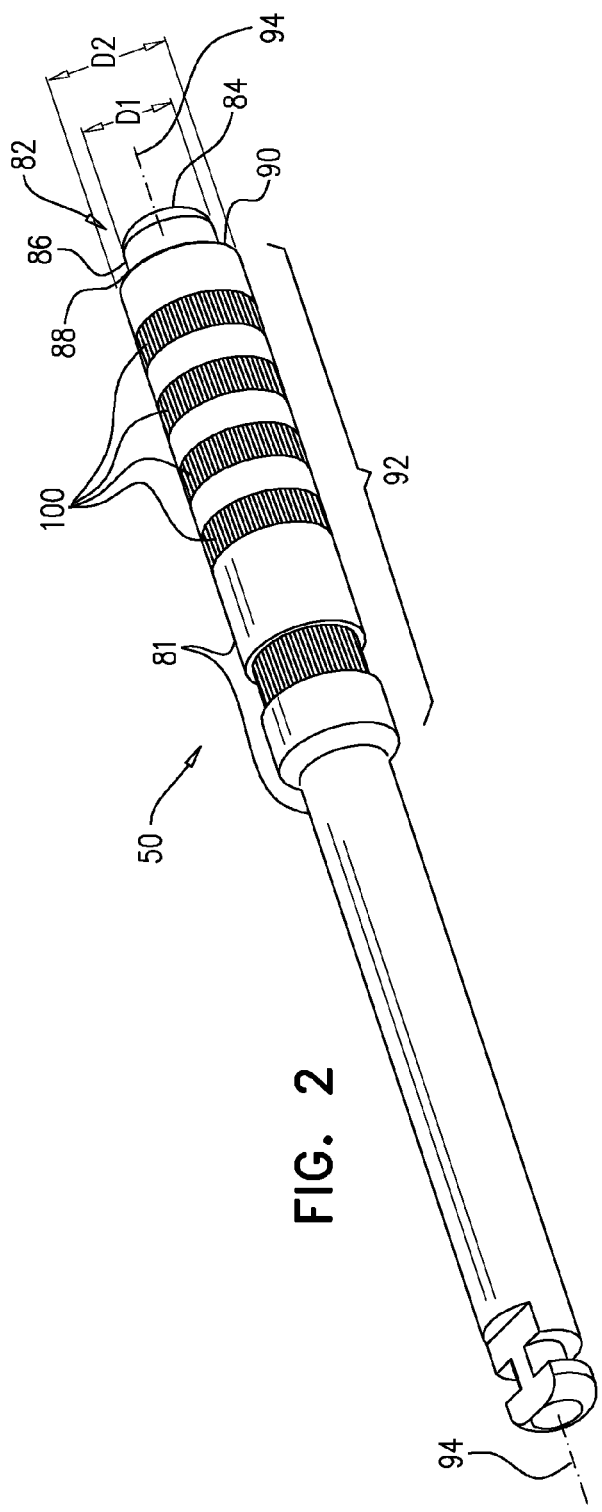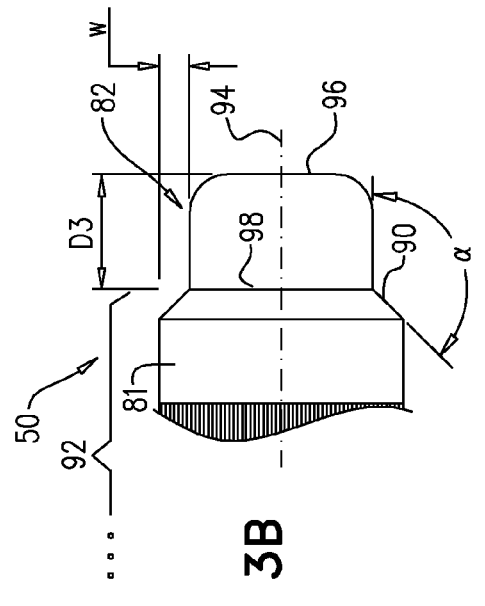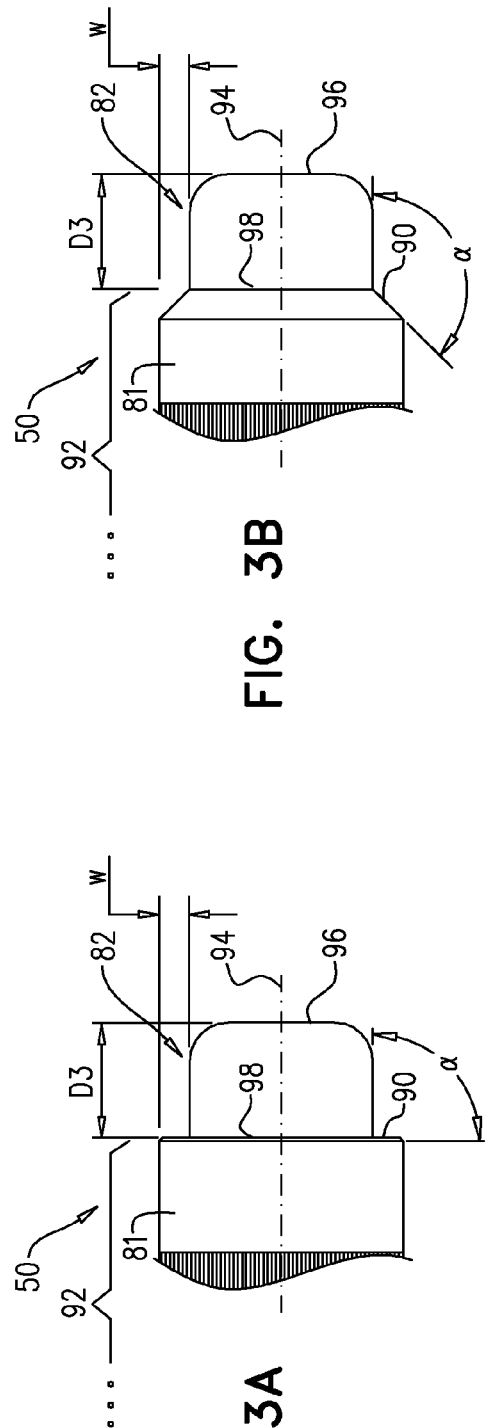

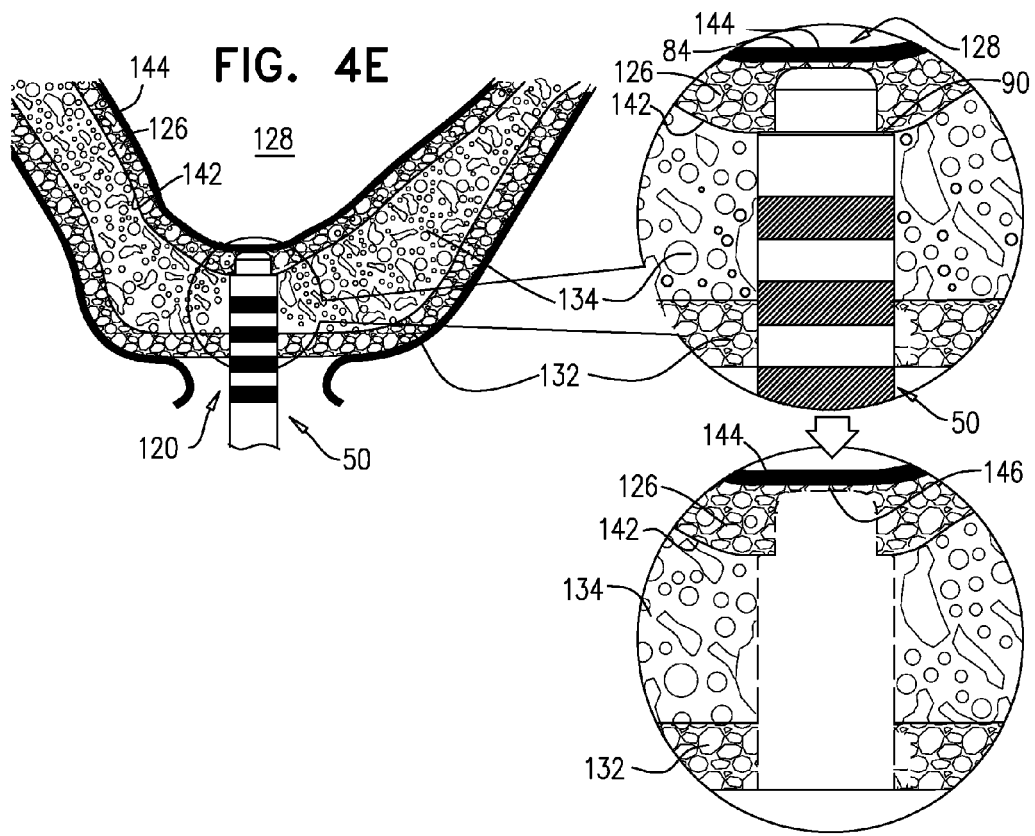
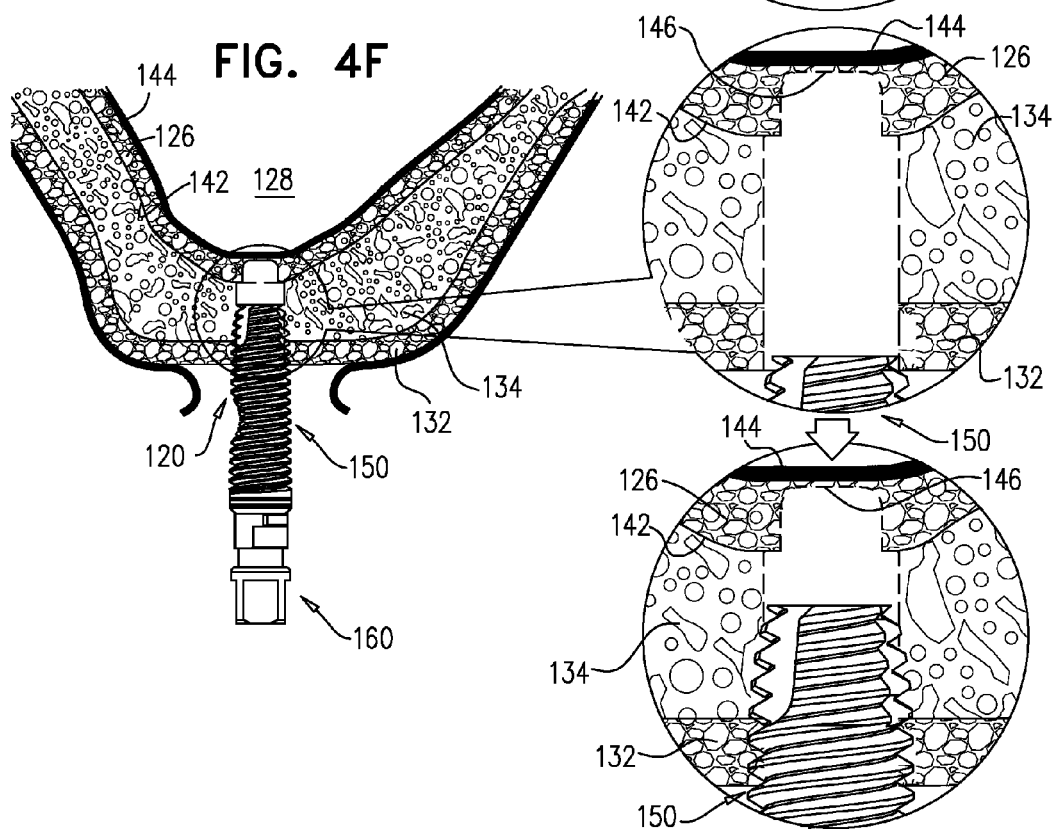

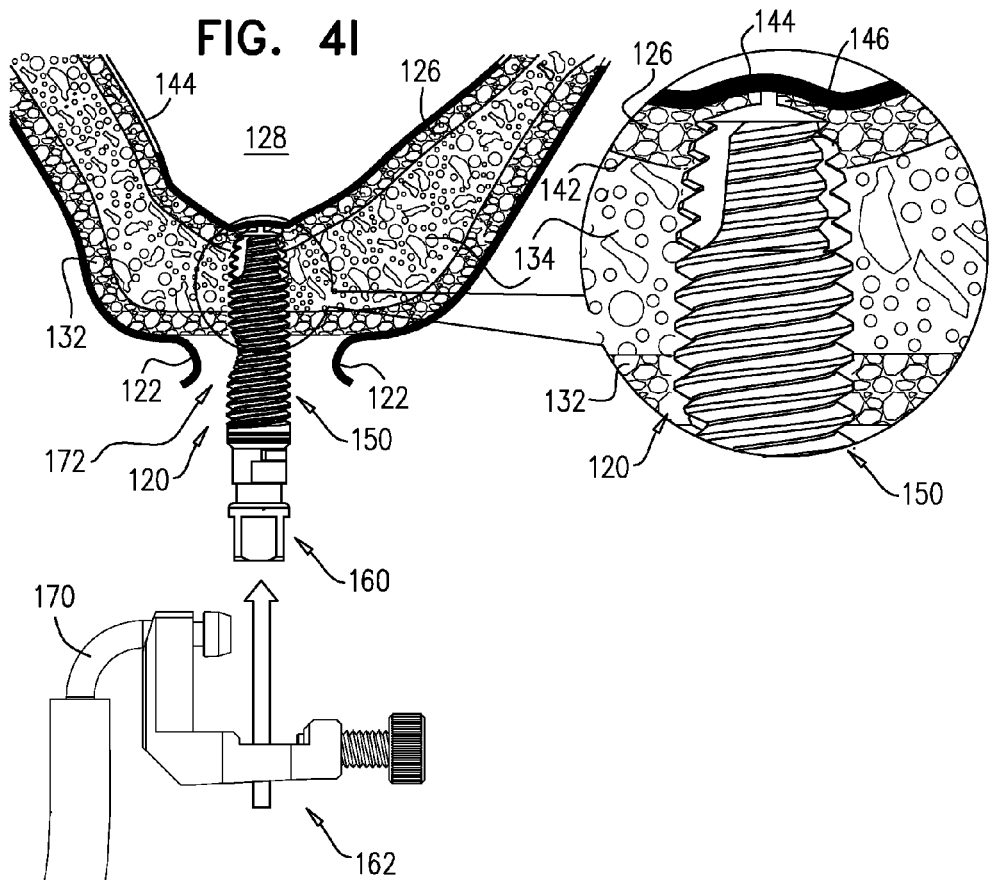
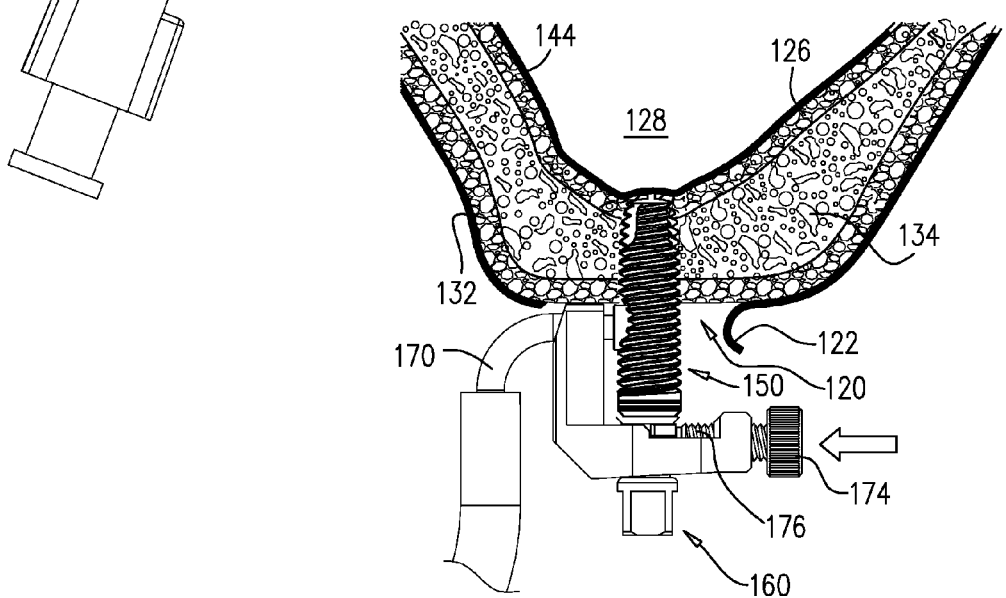

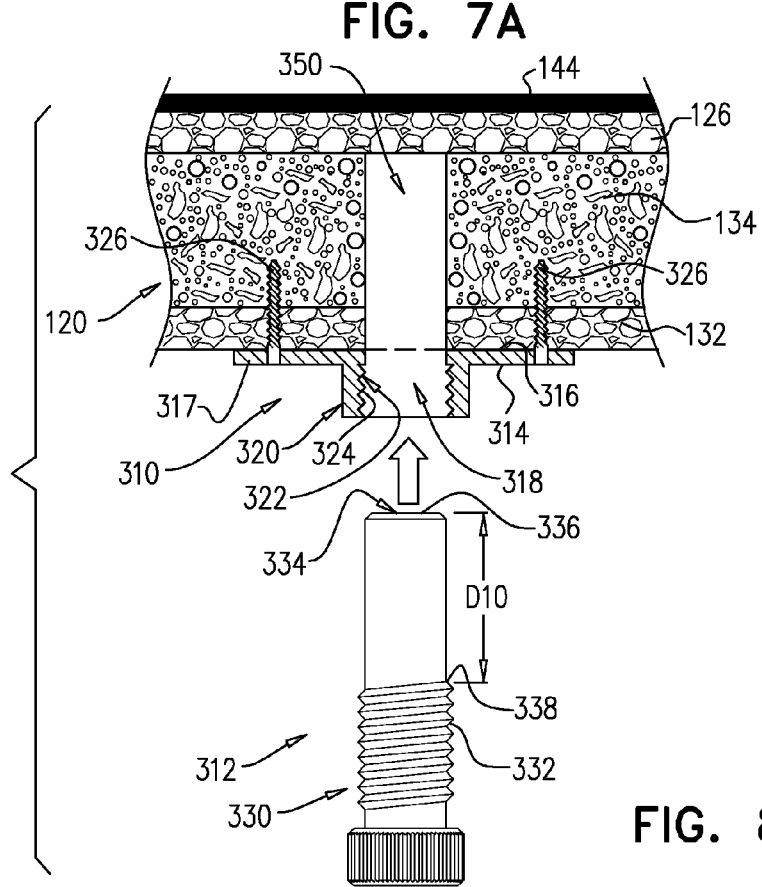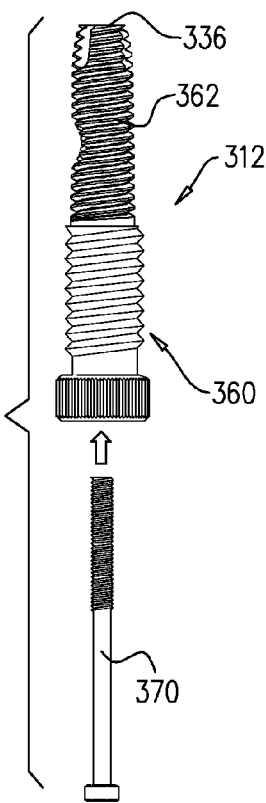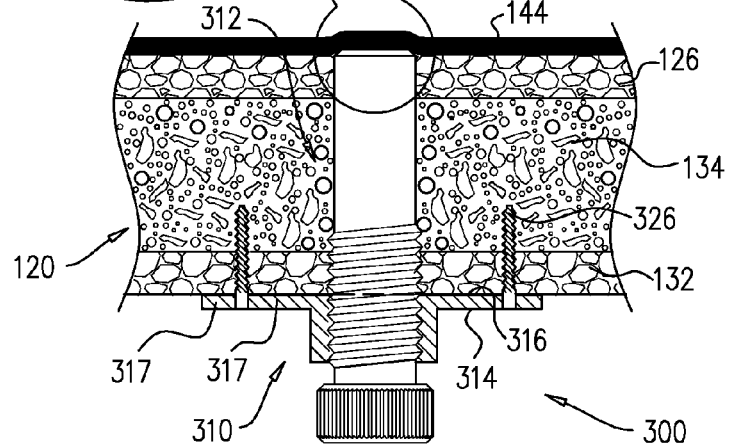

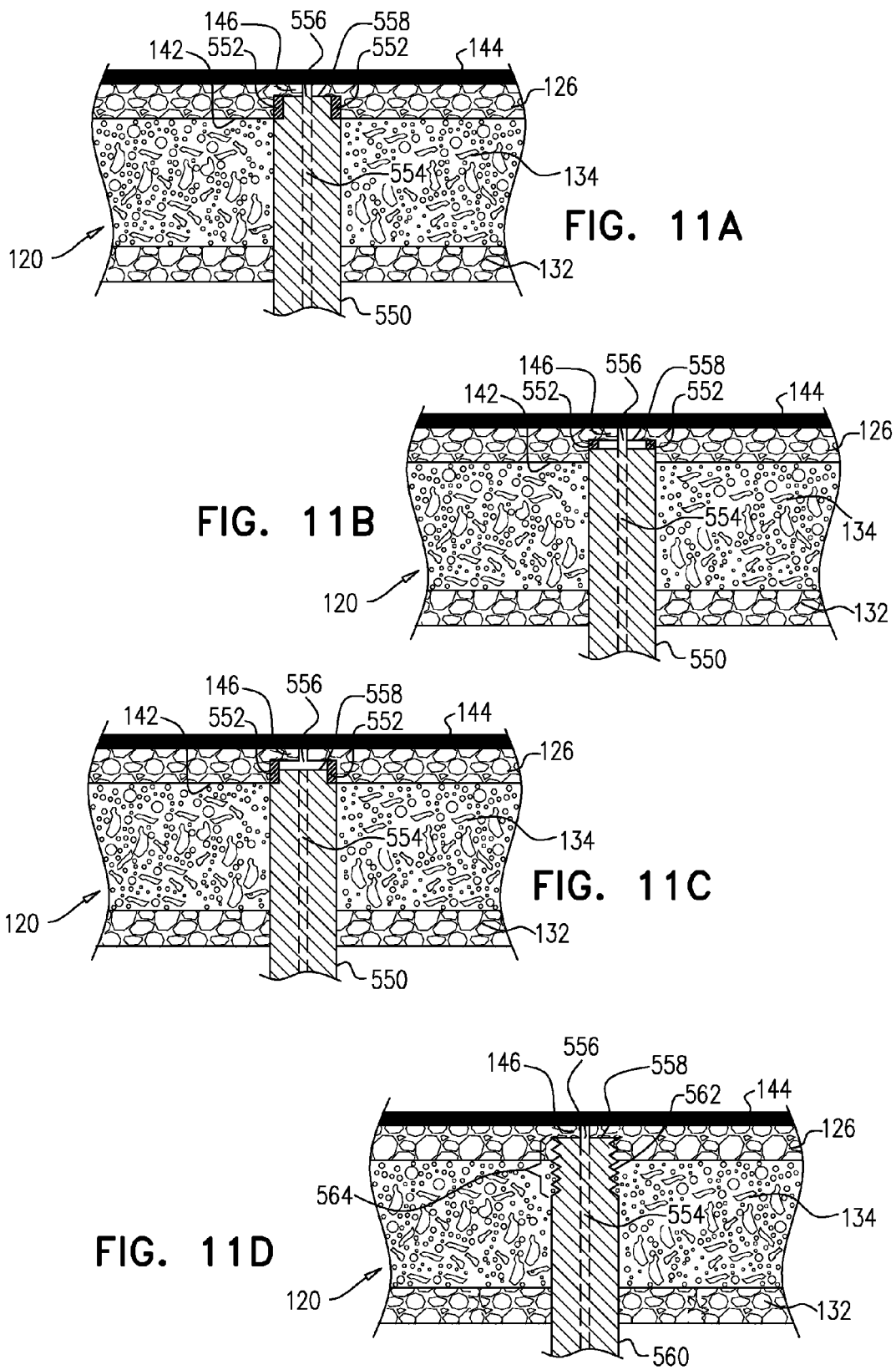

CORTICAL DRILLING

FIELD OF THE INVENTION

The present invention relates generally to dental implants and implantation methods, and specifically to minimally-invasive sinus lift implants and implantation methods.

BACKGROUND OF THE APPLICATION

Osseointegrated dental implants are typically metallic or ceramic screws that are placed in the jawbone for supporting artificial teeth after the loss of natural teeth. Replacement of the maxillary teeth is often a challenging surgical procedure when the remaining maxillary bone has insufficient height to support the implant. One surgical technique for augmenting the maxillary bone includes injecting a regenerative material, such as autogenic, allogeneic, xenogeneic, or synthetic bone graft, into the vicinity of the maxillary bone. The regenerative material forms additional bone mass that integrates with the existing maxillary bone, providing the necessary alveolar height to support the implant.

Bone augmentation procedures are often surgically difficult to perform, and are associated with complications, including infection of the maxillary sinus. The top of the maxillary alveolar ridge forms the floor of the maxillary sinus, and is covered by a thin membrane known as the Schneiderian or subantral membrane. In one surgical procedure, known as a closed or internal sinus lift or elevation procedure, the surgeon drills a bore through the maxillary alveolar ridge from the oral cavity at the desired location of the implant. The bore penetrates the ridge to below the Schneiderian membrane. The surgeon injects the regenerative material through the bore to below the membrane, forming a cavity defined by the top of the ridge and the bottom of the membrane, which cavity occupies a portion of the space initially occupied by the maxillary sinus.

To prevent potentially serious complications, the surgeon must be careful not to perforate the Schneiderian membrane. This is often difficult, because of the delicacy of the membrane, and the restricted access afforded by the closed approach.

SUMMARY OF APPLICATIONS

Some applications of the present invention provided improved tools and drilling techniques for forming an osteotomy in cortical bone, such as for subsequent implantation of a dental implant.

In some applications of the present invention, a minimally-invasive closed sinus lift surgical procedure is provided for implanting a dental implant. The procedure is typically employed when a patient's alveolar maxillary ridge lacks sufficient bone mass to support a conventional dental implant. Typically, the surgeon forms a preparatory osteotomy through the alveolar maxillary ridge toward a superior cortex of a sinus floor. For some applications, in order to form the preparatory osteotomy, the surgeon forms a preliminary bore through an occlusal cortex into trabecular bone of the alveolar ridge. The surgeon optionally widens a portion of the preliminary bore using a counterbore drill. The widened bore serves to position the drill used in the next step of the method. For some applications, no counterbore drill is used when transitioning between different diameter drills.

The surgeon then advances another drill in the preliminary bore. Typically, the surgeon ceases advancing this drill when a distal end of the drill reaches an occlusal surface of the superior cortex of the alveolar ridge, such that the preparatory osteotomy is formed through trabecular bone up to, but not into, the superior cortex. If necessary, advancing this drill lengthens the preliminary bore. For some applications, this second drill has a flat distal cutting edge. The flat distal cutting edge generally provides a sharp, rapid change in resistance when the distal end of the drill comes in contact with the hard superior cortex. The surgeon can readily feel this sharp change in resistance, in order to identify when to cease advancing the drill. (In contrast, if the drill were pointed, the sensed transition would be more gradual.) For some applications, the increased in resistance is identified by a torque measurement in the drilling unit. If the preliminary bore initially has a curved bore end (such as a conical bore end), the flat distal cutting edge also flattens the bore end.

The surgeon subsequently weakens the superior cortex using a cortex drill, which is shaped so as to define a shaft and a cutting protrusion that is coaxial with the shaft. The cutting protrusion defines at least a distal cutting surface, which is configured to cut through cortical bone. For some applications, the distal cutting surface comprises an abrasive surface, such as a diamond bur. The cutting protrusion extends distally from the shaft at an interface that defines a shoulder. The shoulder does not define a cutting surface, such that the shoulder is not configured to cut into cortical bone. The shoulder thus stops advancement of the drill when the shoulder comes in contact with cortical bone. Alternatively, the shoulder slows but does not stop the advancement of the drill. For some applications, the surgeon uses visually-sensible fiducial designators distributed along the shaft to gauge the depth of penetration of the drill into the cortex.

In order to weaken the superior cortex, the surgeon inserts and advances the cortex drill in the preparatory osteotomy such that the distal cutting surface cuts into the superior cortex. The distal cutting surface is configured to cut into (e.g., abrade) the superior cortex to a determined depth, generally without penetrating beyond the superior cortex into a Schneiderian membrane. The surgeon ceases advancing the cortex drill when the shoulder reaches an end of the preparatory osteotomy. The shoulder thus prevents the cutting protrusion from advancing into the superior cortex more than the distance by which the cutting protrusion extends beyond the distal end of the shaft of the cortex drill. Typically, upon the conclusion of this step of the procedure, a portion of the superior cortex remains between a distal-most portion of the cutting protrusion and the Schneiderian membrane. The surgeon withdraws the cortex drill from the alveolar ridge.

Cutting with the cortex drill weakens the superior cortex sufficiently to enable a dental implement to readily break through the remaining portion of the superior cortex. Without this weakening, it is sometimes difficult to achieve sufficient mechanical support from the relatively thin occlusal cortex to enable a tool or implant to cut through the hard superior cortical bone. In addition, the cutting in the cortex forms a round bore that subsequently allows the dental implement (e.g., dental implant or tool) to engage a distal thread thereof solidly in the hard cortical bone. Such engagement improves the traction of the dental implement and allows the implement to press more easily against the residual cortex in order to break the residual cortex. In addition, such engagement allows the formation of a liquid seal that facilitates the subsequent injection of fluids to the sub-membrane space without leakage into the trabecular bone or out back through the osteotomy.

If, as generally occurs, the cortex drill did not cut completely through the superior cortex, the surgeon cuts through (e.g., cracks through) the superior cortex, using a dental implement other than the cortex drill. For some applications, the dental implement is a dental implant. Typically, rotation of the dental implant advances the implant into the preparatory osteotomy and causes the implant to cut through the remaining portion of the superior cortex. Typically, a distal end of the dental implant is shaped so as to define a cutting surface (e.g., a milling surface), which is used to cut through the superior cortex. The milling surface generally pushes bone forward into the Schneiderian membrane. As a result, any sharp surface that may be defined by the edge of flat distal the cutting surface is unlikely to damage the Schneiderian membrane.

For applications in which the dental implant is shaped so as to define a lumen therethrough that opens through a distal external surface, the surgeon attaches an applicator to a proximal end of the dental implant. The surgeon couples a retaining assembly to the applicator, and deploys the retaining assembly such that the retaining assembly sealingly couples a delivery tube to a lateral opening of the implant. The surgeon gently lifts and separates the Schneiderian membrane from the top of the maxillary ridge into a maxillary sinus. In order to do so, the surgeon injects a fluid from a fluid source, via the delivery tube and the lumen of the implant, so as to form a cavity in the maxillary sinus under the membrane between the ridge and the membrane. Typically, the fluid is a biocompatible solution such as normal saline solution, a gel, or a gas. For some applications, the fluid is a therapeutic fluid, or a therapeutic fluid may be introduced after introducing the first fluid. For example, the fluid may be an antiseptic, such as chlorhexidine gluconate, for preventing infection in the sinus. Alternatively or additionally, the fluid may be an anesthetic. The fluid may include a component that helps identify leakage, such as leakage through a damaged Schneiderian membrane into the nose. For example, such a component may comprise a pigment or a biochemically identifiable material such as glucose.

The fluid is typically drained from the cavity, and the surgeon injects a regenerative material, such as liquid or gel bone graft, into the cavity. The surgeon decouples the delivery tube from the implant, and the retaining assembly from the applicator.

The surgeon further advances the implant into the regenerative material in the cavity, and detaches the applicator from the implant. The implant is advanced at least until the lateral opening of the implant is positioned entirely within the bore in the ridge and/or in the regenerative material in the cavity. Such positioning of both ends of the lumen of the implant within bone substantially reduces the risk of infection, because the proximal end of the implant that is exposed to the oral cavity or gingiva is permanently closed. Typically, the surgeon couples a cover screw to the proximal end of the implant using a hand driver, and sutures the gingiva.

Alternatively, the dental implement is a dental tool, such as an osteotome (e.g., a liquid osteotome), which is used to cut through, e.g., crack or fracture, the remaining portion of superior cortex.

In some applications of the present invention, a dental system is provided for performing a stent-assisted sinus lift procedure. The dental system comprises a surgical guide stent and a dental implement. The dental system allows the screwing of a dental implement into an osteotomy, and removal of the implement from the osteotomy, without damaging the internal wall of the osteotomy or the occlusal cortex.

The surgical guide stent has proximal and distal surfaces, and is shaped so as to define a frame that defines an opening. The surgical guide stent comprises a support element, which is shaped so as to define a cylindrical inner surface. The support element is aligned with the opening and extends proximally away from the opening. The cylindrical surface is shaped so as to define an internal thread. For some applications, the surgical guide stent is customized for each individual patient's alveolar ridge. Typically, the dental system further comprises a plurality of fixation elements, which are configured to couple the surgical guide stent to the occlusal surface of the occlusal cortex. Alternatively or additionally, the surgical stent guide is customized and fit to the external contour of the gingiva, with optional fixation elements that penetrate the gingiva into the bone or are affixed to (e.g., cover) adjacent teeth.

The dental implement has an outer surface, a portion of which is shaped so as to define an external thread that is configured to engage the internal thread of the cylindrical surface of the support element. The dental implement has a distal end that is shaped so as to define a cutting surface. For some applications, the dental implement comprises a dental osteotome, dental drill, or other dental tool.

During a procedure using the dental system, the surgeon couples the support element to the occlusal surface of the alveolar ridge, such that the support element extends proximally away from the alveolar ridge. Before or after coupling the support element to the occlusal surface, the surgeon forms, using a cutting tool, an osteotomy through the occlusal cortex into trabecular bone of the alveolar ridge toward a maxillary sinus, without reaching the Schneiderian membrane.

After coupling the support element to the occlusal surface, the surgeon engages, with the internal thread of the cylindrical inner surface of the support element, the external thread defined by the outer surface of a portion of dental implement (other than the cutting tool). While the dental implement is engaged with the cylindrical surface, the surgeon rotates the dental implement such that the dental implement advances into the osteotomy. The surgeon cuts, e.g., breaks, the superior cortex of the alveolar ridge using the dental implement.

The support element, rather than the occlusal cortex and trabecular bone, provides most of the mechanical support for the rotation of the dental implement. As a result, the rotation of dental implement does not weaken the occlusal cortex or trabecular bone.

Optionally, the surgeon uses the dental implement to elevate the Schneiderian membrane and/or to insert a regenerative material into a cavity formed under the Schneiderian membrane, such as described hereinabove. The surgeon removes the dental implement from the osteotomy and decouples the support element from the occlusal surface of the occlusal cortex. Optionally, the surgeon inserts a dental implant into the completed osteotomy; the dental implant need not be shaped so as to define a cutting surface.

In some applications of the present invention, a dental system is provided that comprises an osteotomy sheath and an osteotome. An inner surface of the sheath is shaped so as to define an internal thread. The osteotome is shaped so as to define a shaft having an external thread, and a cutting surface, such as a cracking tip, at a distal end of the osteotome. The external and internal threads are shaped and sized such to engage each another when the osteotome is rotated inside the sheath. Typically, the external and internal threads share a common thread pitch.

During a procedure using the dental system, the surgeon forms an osteotomy in the alveolar ridge through the occlusal cortex into trabecular bone. The surgeon introduces the osteotome into the sheath in the osteotomy. The surgeon rotates the osteotome in the sheath in the osteotomy such that the external thread engages the internal thread and the osteotome advances distally in the sheath at least until the cutting surface cuts into the superior cortex of the alveolar ridge. The surgeon removes the osteotome and the sheath from the osteotomy.

The rotating engagement of the internal and external threads with each other prevents rotation of the sheath with respect to the osteotomy, while still allowing the osteotome to engage the inner wall of the osteotomy. Because the external thread of the osteotome does not directly engage or otherwise come in contact with the bone of the wall of the osteotomy, the thread does not damage the bone.

There is therefore provided, in accordance with an application of the present invention, a method including:

advancing a drill having a distal end through an occlusal cortex into trabecular bone of an alveolar ridge; and ceasing the advancing of the drill when the distal end of the drill reaches an occlusal surface of a superior cortex of the alveolar ridge.

For some applications, the drill has a flat distal cutting edge, and advancing and ceasing advancing include advancing and ceasing advancing the drill having the flat distal cutting edge.

For some applications, the method further includes, before advancing the drill, forming a preliminary bore through the occlusal cortex into the trabecular bone, and advancing the drill includes lengthening the preliminary bore.

For some applications, ceasing the advancing includes ceasing the advancing upon detecting a change in resistance when a distal end of the drill comes in contact with the occlusal surface of the superior cortex. For some applications, detecting the change in resistance includes manually feeling the change in resistance. Alternatively or additionally, for some applications, detecting the change in resistance includes using a tool to measure torque.

For some applications, the drill is a first drill, and further including, after ceasing the advancing, using a second drill to weaken the superior cortex. For some applications, the method further includes, after weakening the superior cortex withdrawing the second drill from the alveolar ridge, and, after withdrawing the second drill, cutting through the superior cortex using a dental implement other than the first drill and the second drill.

For some applications, the drill is a first drill, and the method further includes after ceasing the advancing, cutting into the superior cortex using a distal cutting surface of a cortex drill separate from the first drill, which cortex drill is shaped so as to define a shaft and a cutting protrusion that (a) is coaxial with the shaft and (b) defines at least the distal cutting surface.

For some applications, cutting into the superior cortex includes cutting into the superior cortex using the distal cutting surface of the cortex drill in which the cutting protrusion has a diameter less than that of a portion of the shaft that is proximally adjacent the distal cutting surface, such that the cutting protrusion extends distally from the portion of the shaft at an interface that defines a shoulder, which shoulder does not define a cutting surface. For some applications, the method further includes ceasing cutting into the superior cortex when the shoulder reaches the occlusal surface of the superior cortex. For some applications, the method further includes slowing advancing of the cortex drill into the superior cortex when the shoulder reaches the occlusal surface of the superior cortex. For some applications, cutting into the superior cortex using the distal cutting surface of the cortex drill includes gauging a depth of penetration of the cortex drill into the superior cortex using visually-sensible fiducial designators distributed along the shaft of the cortex drill.

For some applications, cutting into the superior cortex using the distal cutting surface of the cortex drill includes gauging a depth of penetration of the cortex drill into the superior cortex using visually-sensible fiducial designators distributed along the shaft of the cortex drill.

For some applications, the distal cutting surface is an abrasive surface, and cutting into the superior cortex using the distal cutting surface of the cortex drill includes abrading the occlusal surface of the superior cortex using the distal cutting surface.

For some applications, the method further includes, after cutting into the superior cortex using the distal cutting surface of the cortex drill withdrawing the cortex drill from the alveolar ridge, and, after withdrawing the cortex drill, cutting through the superior cortex using a dental implement other than the first drill and the cortex drill. For some applications, cutting through the superior cortex using the dental implement includes cracking the superior cortex using the dental implement. For some applications, the dental implement is a dental implant, and cutting through the superior cortex using the dental implement includes cutting through the superior cortex using the dental implant. For some applications, a distal end of the dental implant is shaped so as to define a cutting surface, and cutting through the superior cortex includes cutting through the superior cortex using the cutting surface of the dental implant. For some applications, the dental implement is a dental osteotome, and cutting through the superior cortex using the dental implement includes cutting through the superior cortex using the dental osteotome.

For some applications, the method further includes, before advancing the drill, forming a preliminary bore through the occlusal cortex into the trabecular bone using a dental twist drill.

For some applications, the method further includes, before advancing the drill, forming a preliminary bore through the occlusal cortex into the trabecular bone by initially forming the preliminary bore having a first diameter, and thereafter, using a counterbore drill, widening a distal portion of the preliminary bore to a second diameter greater than the first diameter.

There is further provided, in accordance with an application of the present invention, apparatus including a dental surgical kit, which includes:

at least one flat drill that is shaped so as to define a flat distal cutting edge, which flat drill is configured to be advanced through an occlusal cortex into trabecular bone of an alveolar ridge until a distal end of the flat drill reaches an occlusal surface of the superior cortex; and at least one cortex drill, which is shaped so as to define (a) a shaft and (b) a cutting protrusion that (i) is coaxial with the shaft and (ii) defines at least a distal cutting surface that is configured to cut into the superior cortex.

For some applications, the cutting protrusion has a diameter less than a diameter of a portion of the shaft that is proximally adjacent the distal cutting surface, such that the cutting protrusion and extends distally from the portion of the shaft at an interface that defines a shoulder, which shoulder does not define a cutting surface. For some applications, a diameter of the flat drill is within +/−10% of the diameter of the portion of the shaft that is proximally adjacent the distal cutting surface of the cortex drill.

For some applications, the cortex drill includes visually-sensible fiducial designators distributed along the shaft of the cortex drill.

For some applications, the distal cutting surface includes an abrasive surface, which may, for example, include a diamond bur.

For some applications, a distal-most portion of the cutting protrusion extends at least 0.5 mm distally beyond a distal end of the shaft.

For some applications, the distal cutting surface is configured to crack bone.

For some applications, the apparatus further includes, in addition to and separate from the cortex drill and the flat drill, a dental implement, which is shaped so as to define a cutting surface at a distal end thereof. For some applications, the dental implement is shaped so as to define a lumen therethrough, a distal end of which lumen opens through at least one distal opening on a distal end of the dental implement. For some applications, the dental implement includes a dental implant. Alternatively, for some applications, the dental implement includes a dental osteotome.

There is still further provided, in accordance with an application of the present invention, apparatus including a cortex drill, which is shaped so as to define:
 a shaft; and
 a cutting protrusion that:
  is coaxial with the shaft,
  defines at least a distal cutting surface,
  has a diameter less than that of a portion of the shaft that is proximally adjacent the distal cutting surface, such that the cutting protrusion and extends distally from the portion of the shaft at an interface that defines a shoulder, which shoulder does not define a cutting surface.

For some applications, the shoulder has a width, measured radially outward from a central longitudinal axis of the portion of the shaft, of between 0.2 and 3 mm. For some applications, the distal cutting surface includes an abrasive surface.

There is additionally provided, in accordance with an application of the present invention, a method including:
 forming a preliminary bore having a first diameter through an occlusal cortex into trabecular bone of an alveolar ridge;
 using a counterbore drill, widening a distal portion of the preliminary bore to a second diameter greater than the first diameter; and
 after widening the portion of the preliminary bore, lengthening the preliminary bore by advancing a second drill having a flat distal cutting edge in the preliminary bore.

For some applications, the second drill has a third greatest outer diameter within 1 mm of the second diameter. For some applications, lengthening the preliminary bore includes ceasing the advancing of the second drill when a distal end of the second drill reaches an occlusal surface of a superior cortex of the alveolar ridge. For some applications, widening the portion of the preliminary bore includes widening a portion of the preliminary bore having a length of at least 0.5 mm.

There is yet additionally provided, in accordance with an application of the present invention, a method including:
 coupling a support element to an occlusal surface an alveolar ridge, such that the support element extends proximally away from the alveolar ridge, which support element is shaped so as to define a cylindrical inner surface;
 before or after coupling the support element to the occlusal surface, forming, using a cutting tool, an osteotomy through an occlusal cortex into trabecular bone of the alveolar ridge toward a maxillary sinus, without reaching a Schneiderian membrane;
 after coupling the support element to the occlusal surface, engaging, with the internal thread of the cylindrical inner surface of the support element, an external thread defined by an outer surface of a portion of a dental implement other than the cutting tool;
 while the dental implement is engaged with the cylindrical surface, rotating the dental implement such that the dental implement advances into the osteotomy;
 cutting through a superior cortex of the alveolar ridge using the dental implement; and
 decoupling the support element from the occlusal surface of the occlusal cortex.

For some applications, coupling the support element to the occlusal surface of the occlusal cortex includes:
 providing a surgical guide stent which has proximal and distal surfaces, and is shaped so as to define an opening, wherein the support element is coupled to the guide stent so as to be aligned with the opening and to extend proximally away from the opening; and
 coupling the guide stent to the occlusal surface of the occlusal cortex, thereby coupling the support element to the occlusal surface.

For some applications, coupling the surgical guide stent includes coupling the surgical guide stent to the occlusal surface by inserting fixation elements into the occlusal cortex at respective locations, each of which is at least 3 mm from a center of a site of the osteotomy.

For some applications, coupling the surgical guide stent to the occlusal surface of the occlusal cortex including customizing the surgical guide stent for the alveolar ridge, and thereafter coupling the surgical guide stent to the occlusal surface of the occlusal cortex.

For some applications, the cutting tool is a dental drill, and forming the osteotomy includes forming the osteotomy using the dental drill. Alternatively, for some applications, the dental implement is a dental osteotome, and the method further includes, after breaking the superior cortex, withdrawing the osteotome from the osteotomy.

For some applications:
 the dental implement includes a dental implant and a tool,
 the outer surface of the portion of the dental implement is an outer surface of a portion of the tool,
 engaging includes engaging the external thread defined by the outer surface of the portion of the tool with the internal thread of the cylindrical inner surface of the support element, while a proximal end of the dental implant is removably coupled to a distal end of the tool,
 breaking the superior cortex includes breaking the superior cortex using the dental implant, and
 the method further includes, after breaking the superior cortex:
  decoupling the tool from the dental implant; and
  withdrawing the tool from the osteotomy and leaving the dental implant in the osteotomy.

For some applications, coupling the support element to the occlusal surface of the alveolar ridge includes coupling the support element to the occlusal surface of the alveolar ridge through gingiva covering the occlusal cortex. Alternatively, coupling the support element to the occlusal surface of the alveolar ridge includes reflecting gingiva covering the alveolar ridge, and thereafter coupling the support element to the exposed occlusal surface of the alveolar ridge.

There is also provided, in accordance with an application of the present invention, apparatus including:
 a surgical guide stent, which (a) has proximal and distal surfaces, (b) is shaped so as to define an opening, and (c) includes a support element, which is shaped so as to define a cylindrical inner surface, which (i) is shaped so as to define an internal thread, and (ii) is aligned with the opening and extends proximally away from the opening; and
 a dental implement, which has (a) an outer surface, a portion of which is shaped so as to define an external thread that is configured to engage the internal thread of the cylindrical surface of the support element, and (b) a distal end that is shaped so as to define a cutting surface.

For some applications, the dental implement includes a dental osteotome.

For some applications:
the dental implement includes a tool and a dental implant, a proximal end of which is removably coupled to a distal end of the tool,
the outer surface of the portion of the dental implement is an outer surface of a portion of the tool, and
the dental implant is shaped so as to define the cutting surface at the distal end of the dental implant.

For some applications, the dental implement further includes an internal screw, and the internal screw, tool, and dental implant are configured such that the internal screw passes through the tool and removably couples the tool to the proximal end of the dental implant, and such that a proximal end of the screw is accessible from a proximal end of the tool when the tool is coupled to the dental implant.

For some applications, the apparatus further includes a plurality of fixation elements, which are configured to couple the surgical guide stent to the occlusal surface of the occlusal cortex.

There is further provided, in accordance with an application of the present invention, a method including:
forming an osteotomy in an alveolar ridge through an occlusal cortex into trabecular bone;
introducing, into the osteotomy, a sheath shaped so as to define an internal thread on an inner surface of the sheath;
introducing, into the sheath in the osteotomy, an osteotome shaped so as to define (a) an external thread on a shaft thereof, and (b) a cutting surface at a distal end of the osteotome;
rotating the osteotome in the sheath in the osteotomy such that the external thread engages in the internal thread and the osteotome advances distally in the sheath at least until the cutting surface cuts into a superior cortex of the alveolar ridge; and
removing the osteotome and the sheath from the osteotomy.

For some applications, the cutting surface is a cracking tip, and rotating includes rotating the osteotome until the cracking tip cracks the superior cortex.

For some applications, the sheath includes rubber, and introducing the sheath includes introducing the rubber sheath. Alternatively or additionally, the sheath includes a metal, and introducing the sheath includes introducing the metal sheath.

For some applications, forming the osteotomy includes forming the osteotomy through the trabecular bone up to, but not into, the superior cortex. For some applications, forming the osteotomy includes forming the osteotomy through the trabecular bone without reaching the superior cortex. For some applications, forming the osteotomy includes forming the osteotomy through the trabecular bone and partially through the superior cortex.

There is still further provided, in accordance with an application of the present invention, apparatus including:
a sheath, an inner surface of which is shaped so as to define an internal thread; and
an osteotome shaped so as to define a shaft having an external thread, and a cutting surface at a distal end of the osteotome,
wherein the external and the internal threads are shaped and sized such to engage each another when the osteotome is rotated inside the sheath.

For some applications, the external and internal threads share a common thread pitch.

For some applications, the cutting surface includes a cracking tip.

For some applications, the sheath includes rubber.

For some applications, the sheath has an inner diameter of between 1 and 5 mm. Alternatively or additionally, for some applications, the sheath has a length of between 2 and 8 mm.

The present invention will be more fully understood from the following detailed description of applications thereof, taken together with the drawings, in which:

BRIEF DESCRIPTION OF THE DRAWINGS

FIG. 2 is a schematic illustration of a cortex drill, in accordance with an application of the present invention;

FIGS. 3A-B are schematic illustrations of a distal portion of the cortex drill of FIG. 2, in accordance with respective applications of the present invention;

FIGS. 7A-B are schematic illustrations of another dental system and a method for its use, in accordance with an application of the present invention;

FIG. 8 is a schematic illustration of another configuration of a dental implement of the dental system of FIGS. 7A-B, in accordance with an application of the present invention;

FIGS. 11A-D are schematic illustration of cortex sealing techniques, in accordance with respective applications of the present invention.

DETAILED DESCRIPTION OF APPLICATIONS

Figure 1:
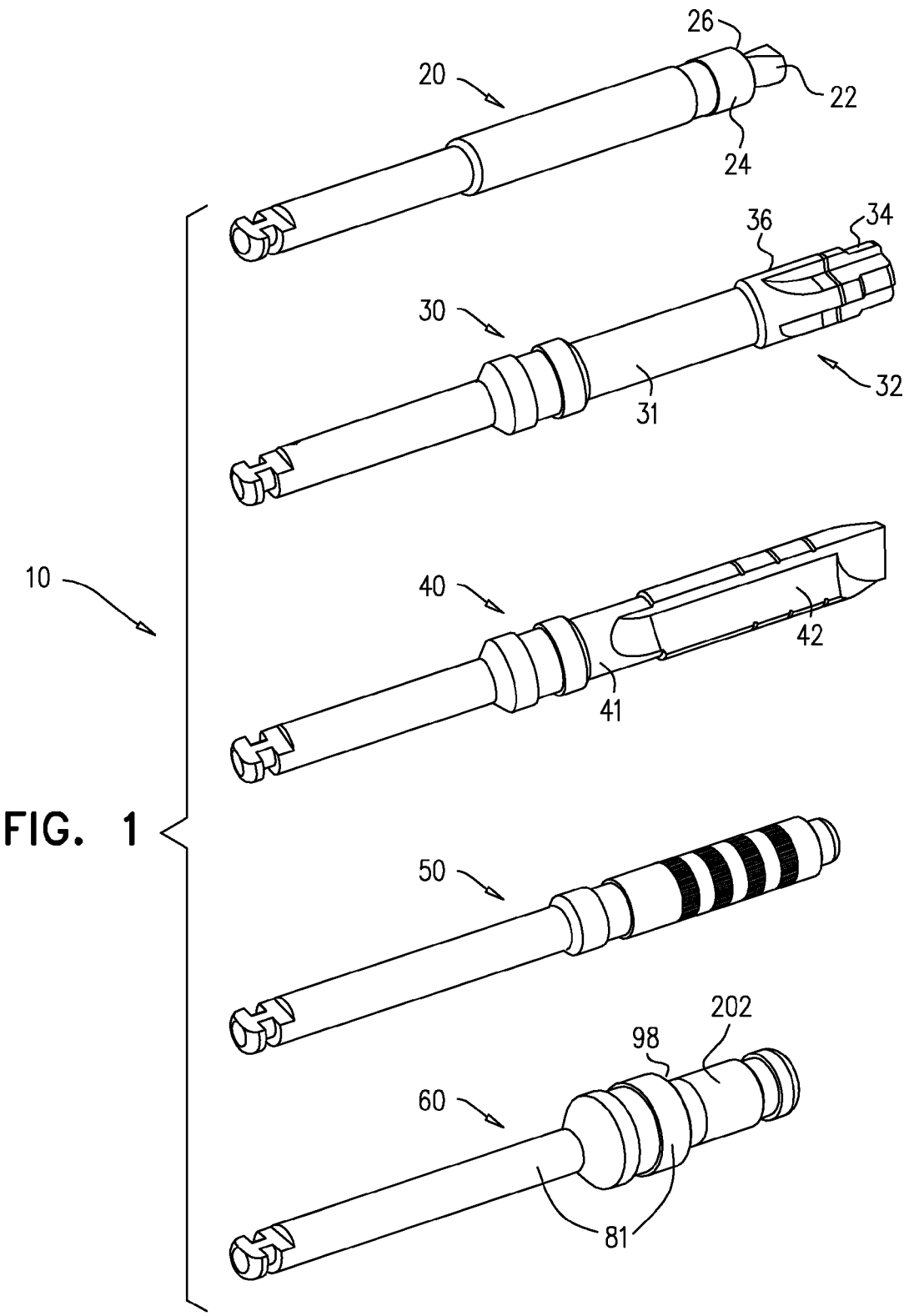
FIG. 1 is a schematic illustration of a set of dental tools, in accordance with an application of the present invention.

FIG. 1 is a schematic illustration of a set 10 of dental tools, in accordance with an application of the present invention. Set 10 or a subset thereof may be used to perform the dental procedures described herein, and/or to perform other dental procedures. Set 10 may include one or more of the following dental tools:
a pilot drill 20, which typically comprises a dental twist drill shaped so as to define a stopper 24. Pilot drill 20 is shaped so as to define a proximal shaft 21, a distal bur 22, and stopper 24 proximal to bur 22. Stopper 24 has a greater diameter than that of bur 22, and defines a shoulder 26 comprising a non-cutting distal surface, which prevents advancement of pilot drill 20 beyond a depth equal to a length of bur 22. Typically, bur 22 has a length of between 2 and 5, such as 3 mm;

a counterbore drill 30, which is shaped so as to define a proximal shaft 31 and a distal bur 32. Distal bur 32 includes distal and proximal portions 34 and 36. Proximal portion 36 is shaped so as to define a cutting surface. A diameter of proximal portion 36 is greater than that of distal portion 34.

a drill 40, which is shaped so as to define a shaft 41 and a flat distal cutting edge 42;

a cortex drill 50, which is described in detail hereinbelow with reference to FIGS. 2 and 3A-B; and/or a cortex drill 60, which is described hereinbelow with reference to FIG. 6A.

The proximal ends of the above-mentioned drills typically have an interface to a dental handpiece (such as a physiodispenser) or a high-speed dental drill. Optionally, the drills may be irrigated, either externally and/or internally. The drills may have depth markings (e.g., laser-etched).

Reference is made to FIG. 2, which is a schematic illustration of cortex drill 50, in accordance with an application of the present invention. Cortex drill 50 is shaped so as to define a shaft 81 and a cutting protrusion 82. Cutting protrusion 82 defines at least a distal cutting surface 84, and, optionally, a lateral cutting surface 86. Typically, distal cutting surface 84 is devoid of large cutting surfaces (and optionally may have a generally blunt outer contour) and includes a portion perpendicular to axis 94, which portion is generally flat or convexly curved.

For some applications, distal cutting surface 84 comprises an abrasive surface, such as a diamond bur, a carbide bur that has a fine mesh of cutting edges (e.g., crisscrossed), or a milling end. Typically, cortex drill 50 cuts by rotating. Alternatively, the drill cuts by moving in a reciprocating motion (back and forth), which may reduce the already low risk of damaging the Schneiderian membrane if the tip of the drill should come into contact with the membrane, as described hereinbelow. Further alternatively, distal cutting surface 84 utilizes non-mechanical means for cutting, such as ultrasound energy, typically generated using one or more piezoelectric transducers.

Cutting protrusion 82 is coaxial with and extends distally from shaft 81 at an interface 88 that defines a shoulder 90. Shoulder 90 does not define a cutting surface, such that the shoulder is not configured to cut into cortical bone. The shoulder thus stops advancement of the drill when the shoulder comes in contact with cortical bone, as described hereinbelow with FIGS. 4E, 6A-B, or 6C. Alternatively or additionally, the shoulder slows advancement of the drill, thereby allowing easy control of penetration depth of the drill, optionally in conjunction with the use of visually-sensible fiducial designators 100, described hereinbelow with reference to FIG. 2. Cutting protrusion 82 has a diameter D1 less than a diameter D2 of a portion 92 of shaft 81 that is proximally adjacent cutting protrusion 82. For example, D1 may be between 1.5 and 4 mm, such as 2.4 or 2.8 mm, and D2 may be between 2 and 6 mm, such as 3.2 or 3.65 mm.

Reference is made to FIGS. 3A-B, which are schematic illustrations of a distal portion of cortex drill 50, in accordance with respective applications of the present invention. Typically shoulder 90 has a width W, measured radially outward from a central longitudinal axis 94 of portion 92 of shaft 81, of at least 0.2 mm, no more than 3 mm, and/or between 0.2 and 3 mm, such as 0.4 mm. A distal-most portion 96 of cutting protrusion 82 extends a distance D3 distally beyond a distal end 98 of shaft 81. For example, distance D3 may be at least 0.5 mm, such as at least 1 mm, e.g., 1.5 mm. Typically, distal-most portion 96 includes a radially-central point of cutting protrusion 82. For some applications, as shown in FIGS. 3A-B, the surface of shoulder 90 is generally flat, while for other applications, the surface of shoulder 90 is curved (configuration not shown).

For some applications, central longitudinal axis 94 and a line defined by a surface of shoulder 90 define an angle α (alpha) therebetween, measured on a distal side of the line, which angle is between 85 and 135 degrees, such as between 85 and 95 degrees, e.g., 90 degrees. In the configuration shown in FIG. 3A (and FIGS. 1, 2, and 4A-N), angle α (alpha) equals 90 degrees. In the configuration shown in FIG. 3B, angle α (alpha) equals about 130 degrees.

Reference is again made to FIG. 2. For some applications, portion 92 of shaft 81 has a plurality of visually-sensible fiducial designators 100, at respective longitudinal locations along portion 92, e.g., at one-millimeter intervals. The dental surgeon may use designators 100 to visually gauge a depth of insertion of the drill in an osteotomy.

For some applications, cortex drill 50 is irrigated, either externally and/or internally. Internal irrigation may decrease the likelihood of damaging the Schneiderian membrane.

Figure 4A:
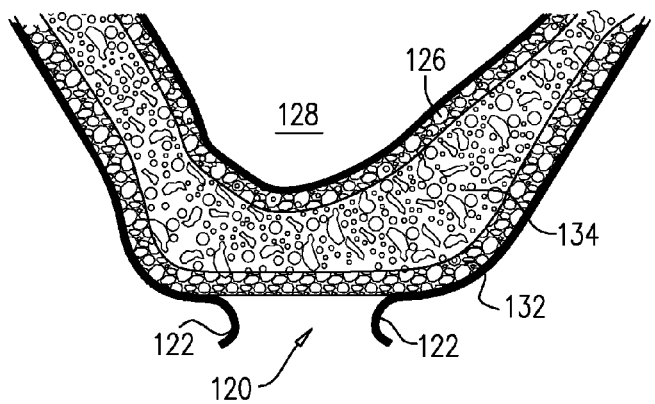
FIGS. 4A-N are schematic illustrations of several steps of a minimally-invasive closed sinus lift surgical procedure for a implanting dental implant, in accordance with an application of the present invention.
Figure 4B:
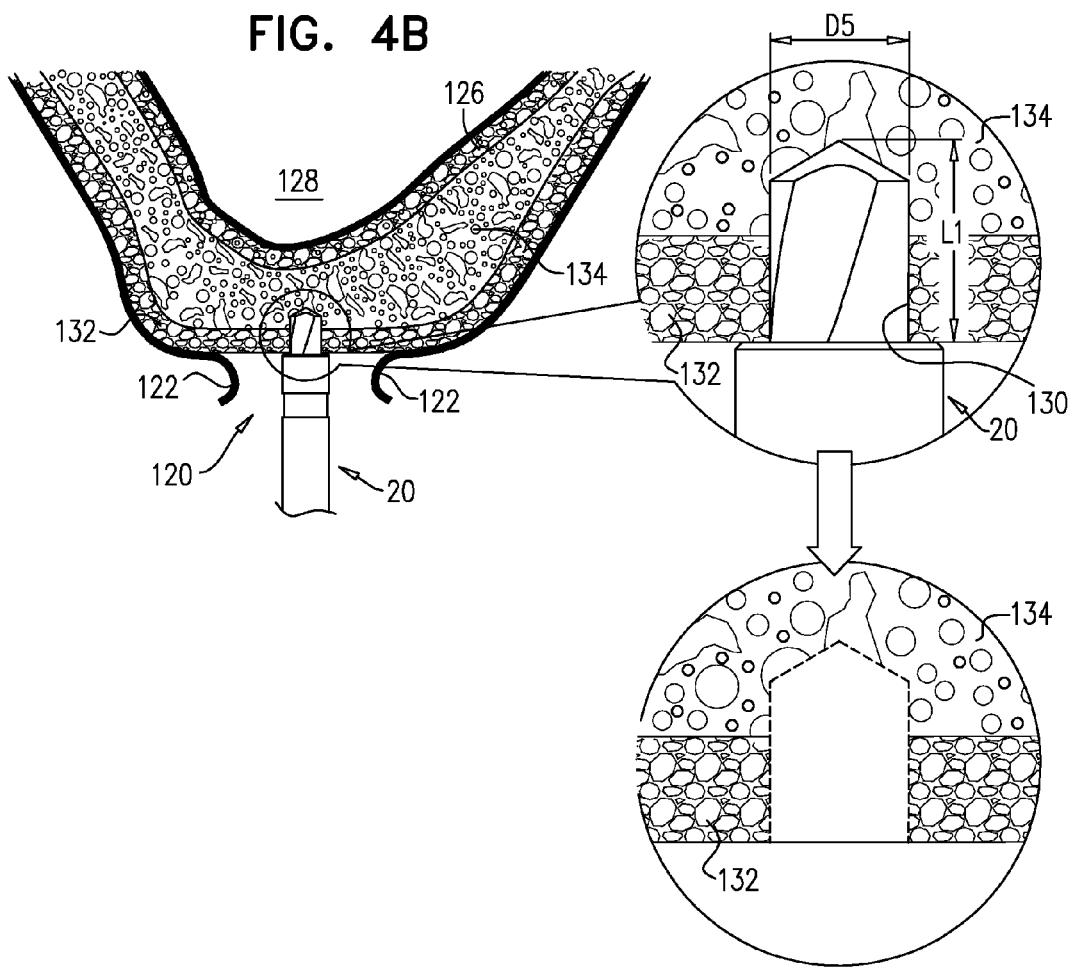
Figure 4C:
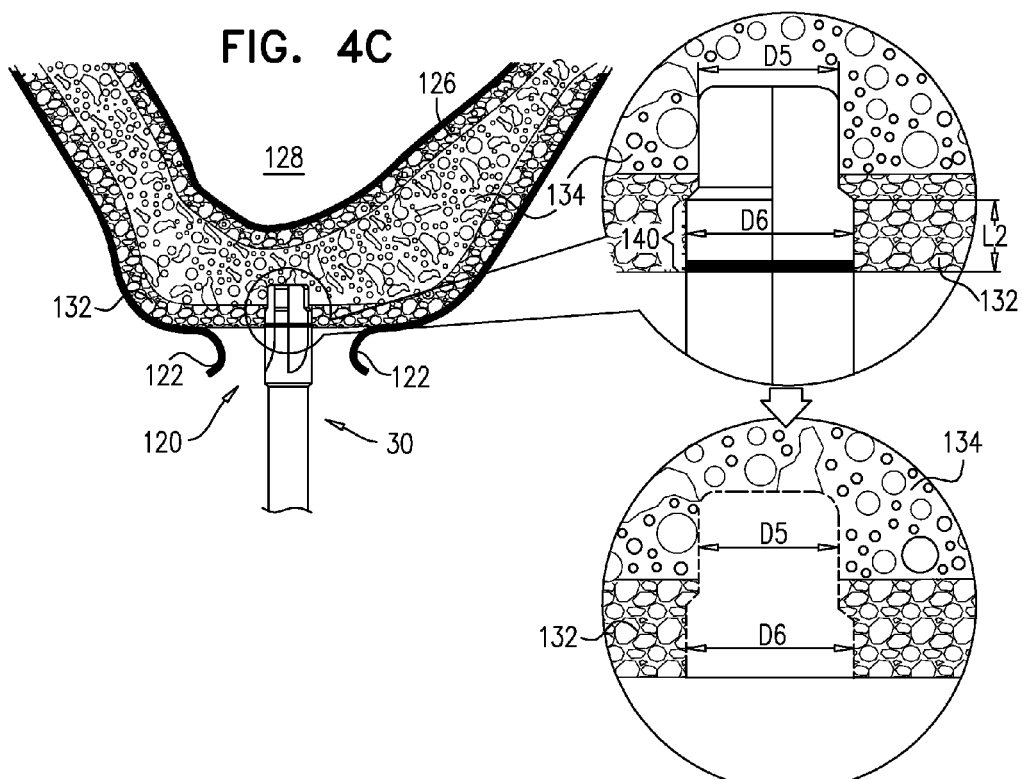
Figure 4D:
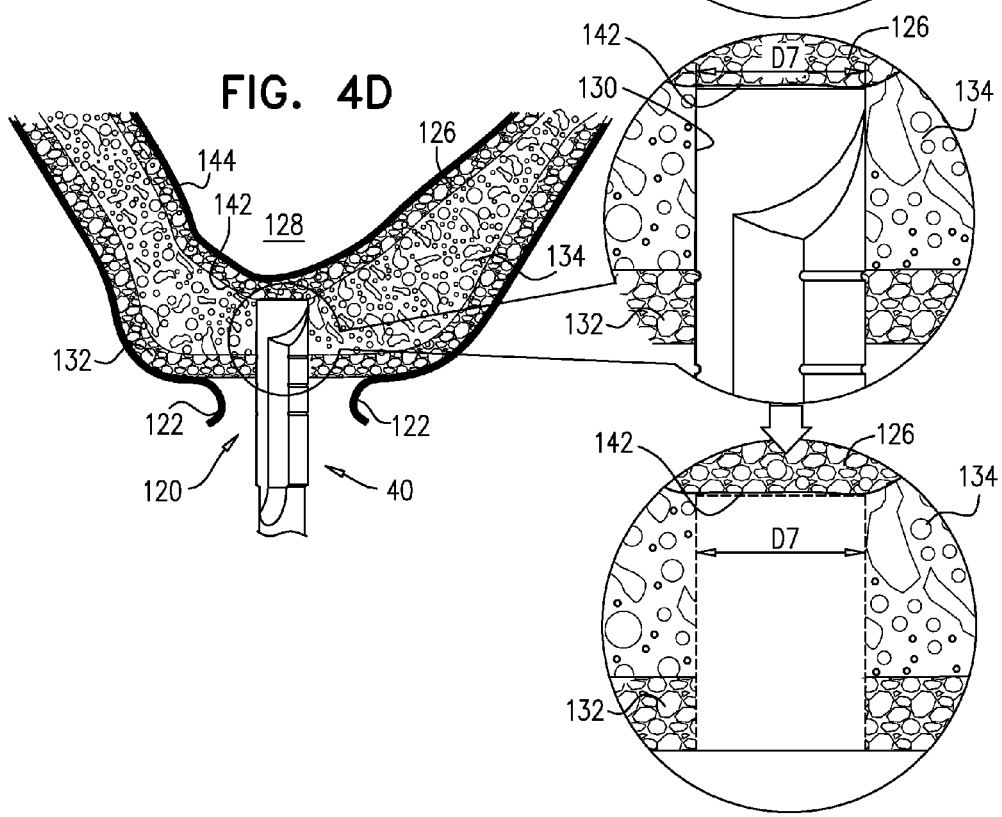
Figure 4G:
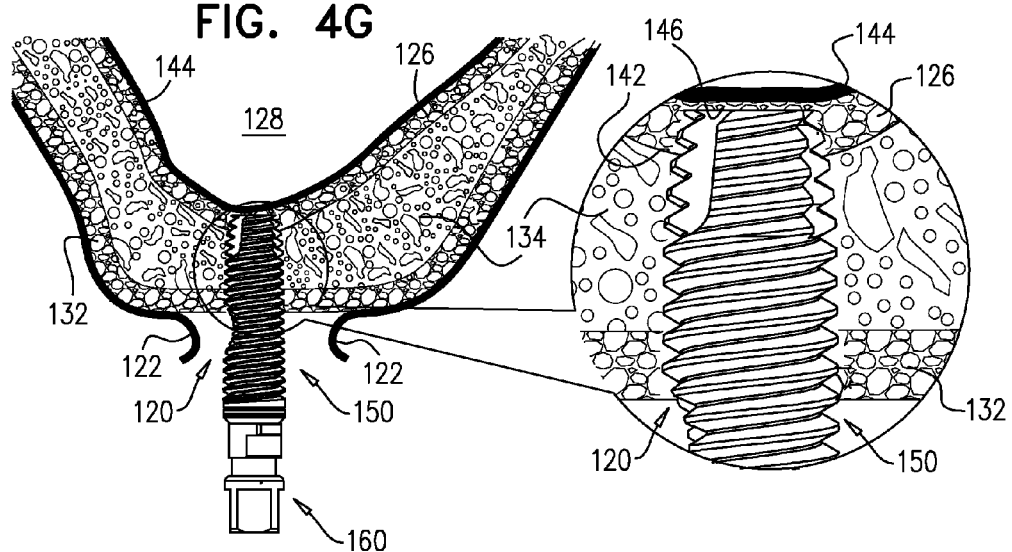
Figure 4H:
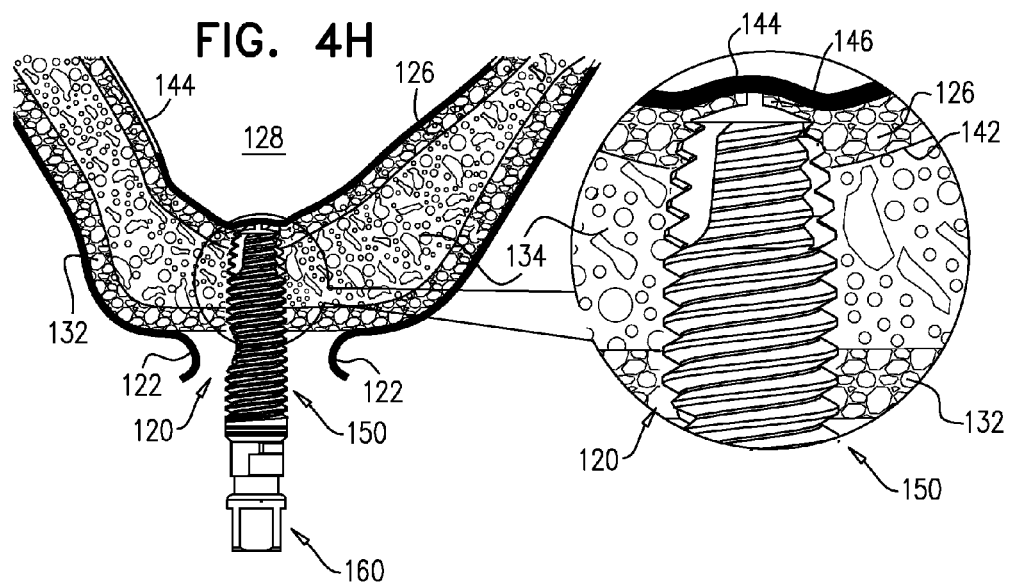
Figure 4K:
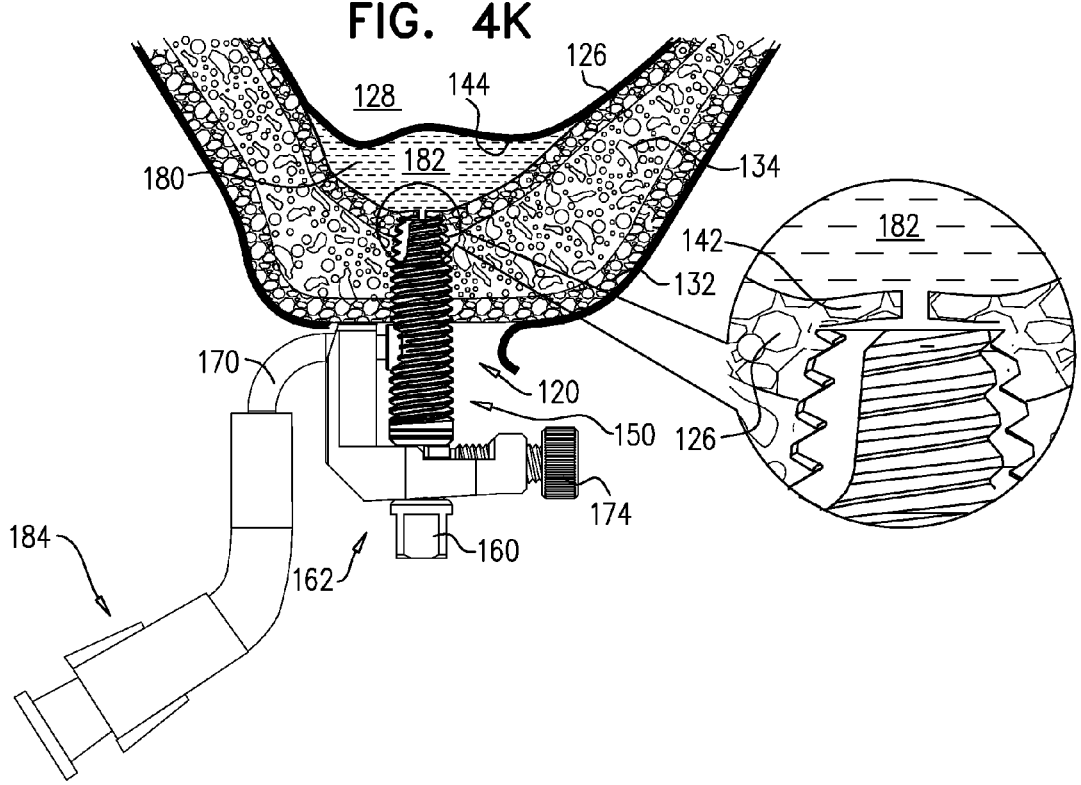
Figure 4L:
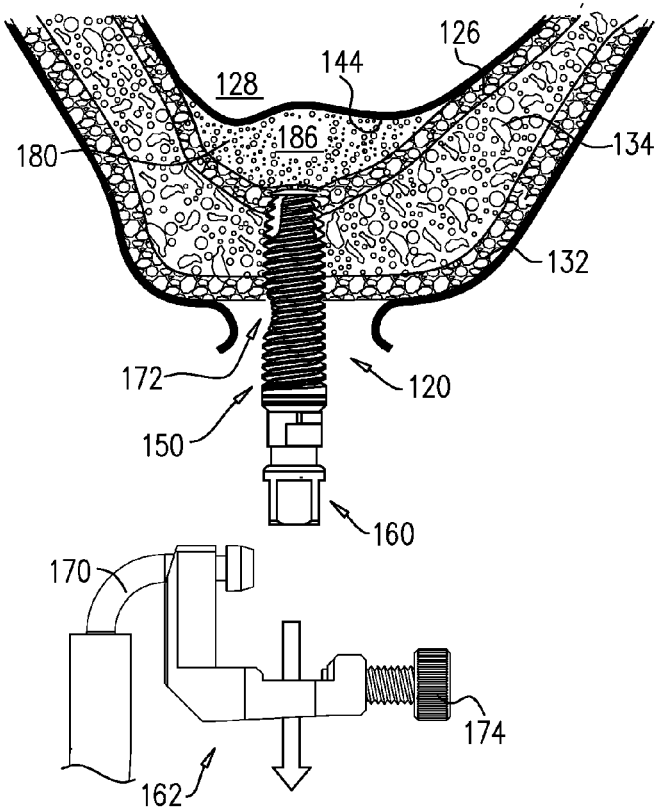
Figure 4N:
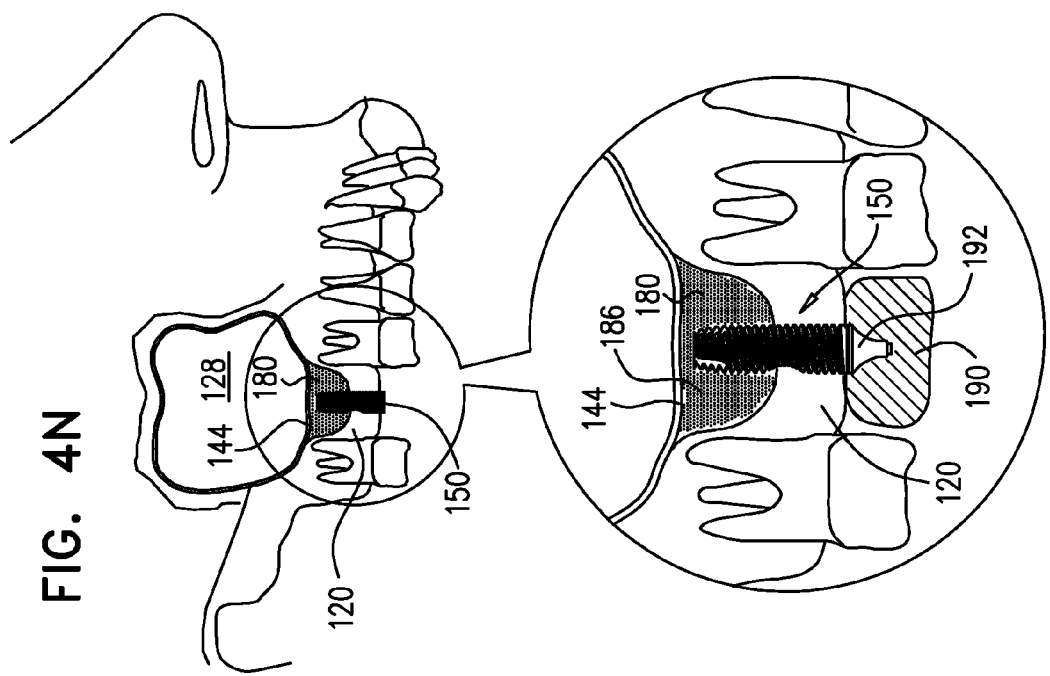

Reference is now made to FIGS. 4A-N, which are schematic illustrations of several steps of a minimally-invasive closed sinus lift surgical procedure for implanting a dental implant, in accordance with an application of the present invention. The procedure is typically employed when a patient's alveolar maxillary ridge 120 lacks sufficient bone mass to support a conventional dental implant. For some applications, the surgical procedure is performed using one of dental surgical kits 200A or 200B, described hereinbelow with reference to FIGS. 5A and 5B, respectively.

A surgeon begins the procedure by preparing the oral facial region, and administering a local anesthetic. As shown in FIG. 4A, the surgeon reflects gingiva 122, exposing an occlusal surface of alveolar ridge 120. Alternatively, the gingiva is not reflected, typically when a surgical stent external to the gingiva is used to guide the drilling.

Typically, the surgeon forms a preparatory osteotomy through alveolar maxillary ridge 120 toward a superior cortex 126 (also known as a sinus cortex) of a sinus floor 128.

For some applications, as shown in FIGS. 4B-D, in order to form the preparatory osteotomy, the surgeon forms a preliminary bore 130 through an occlusal cortex 132 (also known as an inferior cortex and the alveolar cortex) into trabecular bone 134 of alveolar ridge 120, as shown in FIG. 4B. Preliminary bore 130 typically has a first diameter D5 of between 1.5 and 3 mm, such as between 1.8 and 2.0 mm, and a length L1 of between 1 and 4 mm, such as 3 mm. Typically, the surgeon first marks the drilling location using a marking drill, as is known in the art (step not shown). For some applications, the surgeon forms preliminary bore 130 using pilot drill 20, described hereinabove with reference to FIG. 1. As mentioned above, pilot drill 20 is advanced until shoulder 26 thereof comes in contact with the occlusal surface of occlusal cortex 132, thereby stopping further advancement of the drill. For example, the pilot drill may have a diameter of 2.0 mm. Alternatively, the surgeon forms preliminary bore 130 using another dental drill, such as a conventional twist drill.

As shown in FIG. 4C, the surgeon optionally widens a proximal portion 140 of preliminary bore 130 to a second diameter D6 greater than first diameter D5, typically without widening a distal portion of preliminary bore beyond first diameter D5. For some applications, proximal portion 140 is entirely within occlusal cortex 132 (as shown), while for other applications, the proximal portion extends from the occlusal cortex partially into trabecular bone 134 (not shown). The surgeon typically performs this step using a counterbore drill, such as counterbore drill 30, described hereinabove with reference to FIG. 1. The widened bore serves to position the drill used in the next step of the method, described with reference to FIG. 4D. Alternatively, preliminary bore 130 is not widened, and the transition between drills of increasing diameters is performed without widening the diameter of the proximal portion of the osteotomy.

As shown in FIG. 4D, after widening the portion of the preliminary bore, the surgeon advances another drill in preliminary bore 130, such as drill 40, described hereinabove with reference to FIG. 1, or another drill, to form a preparatory osteotomy. Drill 40 has flat distal cutting edge 42. If necessary, advancing this drill into preliminary bore 130 lengthens preliminary bore 130. For applications in which drill 40 is used, the surgeon typically ceases advancing drill 40 when a distal end of drill 40 reaches an occlusal surface 142 of superior cortex 126 of alveolar ridge 120, such that the preparatory osteotomy is formed through trabecular bone 134 up to, but not into, superior cortex 126. Flat distal cutting edge 42 generally provides a sharp, rapid change in resistance when the distal end of drill 40 comes in contact with the hard superior cortex. The surgeon can readily detect this sharp change in resistance, in order to identify when to cease advancing the drill. The increase in resistance may be detected by manually feeling the change in resistance. Alternatively, the increase in resistance may be detected using a tool to measure torque, e.g., by observing an increase in the displayed torque on the drilling unit. (In contrast, if the drill were pointed, the sensed transition would be more gradual.) If preliminary bore 130 initially has a curved bore end, flat distal cutting edge 42 also flattens the bore end. Alternatively, the surgeon does not advance drill 40 all of the way to superior cortex 126. At this stage of the procedure, it is typically not desirable to cut into the superior cortex. However, the surgeon may sometimes form the preparatory osteotomy through trabecular bone 134 and partially through superior cortex 126. Typically, drill 40 has a greatest outer diameter D7 within 1 mm of second diameter D6, i.e., equal to D6 +/−1 mm.

Depending on the surgical plan for the particular patient, the surgeon may repeat the widening steps described above with reference to FIGS. 4C and 4D two or three times. For example, the widening steps may first be performed with (a) a counterbore drill 30, portions 34 and 36 of which have, for example, diameters of 2.0 and 2.8 mm, respectively, and (b) a drill 40 having a diameter of, for example, 2.8 mm. If additional widening is required, the widening steps of FIGS. 4C and 4D may be repeated with (a) a wider counterbore drill 30, portions 34 and 36 of which have, for example, diameters of 2.8 and 3.2 mm, respectively, and (b) a wider drill 40 having a diameter of, for example, 3.2 mm. If still more widening is required, the widening of steps of FIGS. 4C and 4D may be repeated yet again with (a) a still wider counterbore drill 30, portions 34 and 36 of which have, for example, diameters of 3.2 and 3.65 mm, respectively, and (b) a still wider drill 40 having a diameter of, for example, 3.65 mm. Alternatively, the widening may be performed without using a counterbore drill between the successive drill diameters.

When completely formed, the preparatory osteotomy typically has a diameter of between 2 and 7 mm, e.g., between 3 and 6 mm, such as either 3.2 or 3.65 mm, and leaves residual bone thickness of between 0 and 2 mm, e.g., between 0.5 and 1.5 mm. The preparatory osteotomy may be measured using techniques known in the art, such as CT, x-ray, or x-ray with a depth guide. For some applications, a surgical guide is used to ensure clearance between the center of the osteotomy and the nearest tooth surfaces. Optionally, a pre-surgery radiograph (e.g., CT or x-ray) is performed, in order to enable the surgeon to estimate the height of the residual bone and plan the osteotomy accordingly.

The surgeon subsequently weakens superior cortex 126 using cortex drill 50, as shown in FIG. 4E. This weakening step is performed after the last widening iteration described above with reference to FIGS. 4C and 4D. For example, shaft 81 of cortex drill 50 may have a diameter of 3.2 mm or 3.65 mm. This step may also optionally be additionally performed after an earlier widening step, such as after the middle widening step if three widening steps are performed.

The surgeon inserts cortex drill 50, described hereinabove with reference to FIGS. 2 and 3A-B, into the preparatory osteotomy. In order to weaken superior cortex 126, the surgeon advances cortex drill 50 in the preparatory osteotomy such that distal cutting surface 84 cuts into superior cortex 126 of alveolar ridge 120. Distal cutting surface 84 is configured to cut into (e.g., abrade) superior cortex 126 to a determined (optionally, predetermined) depth, generally without penetrating beyond the superior cortex into a Schneiderian membrane 144. The depth is typically between 0.5 and 2 mm. However, because distal cutting surface 84 is typically devoid of large cutting surfaces (and optionally may have a generally blunt outer contour), even if the cutting surface penetrates beyond the superior cortex, the cutting surface generally does not perforate or otherwise damage the Schneiderian membrane, but instead gently pushes against the membrane. Typically, portion 92 of shaft 81 of cortex drill 50 has a diameter approximately equal to a diameter of the preparatory osteotomy, to minimize lateral movement of cortex drill 50 in the osteotomy. Typically, a diameter of the flat drill is approximately equal (e.g., within +/−100) of diameter D2 of portion 92 of shaft 81 that is proximally adjacent to cutting protrusion 82 of cortex drill 50 (see FIGS. 2 and 3A-B).

The surgeon ceases advancing cortex drill 50 when shoulder 90 reaches an end of the preparatory osteotomy. For some applications, the surgeon ceases advancing in response to a sensed contact of the shoulder with occlusal surface 142 of superior cortex 126 (e.g., sensed manually, or using a sensor element). The shoulder thus prevents cutting protrusion 82 from advancing into superior cortex 126 more than distance D3, described hereinabove with reference to FIGS. 3A-B. Because shoulder 90 does not define a cutting surface, the shoulder does not cut into occlusal surface 142, and is thus blocked from further advancement by the occlusal surface. Alternatively, shoulder 90 impedes and/or slows but does not block the advancement of the drill into the cortex. The surgeon may use fiducial designators 100 (optionally, in combination with the slowed progress) to accurately gauge the depth of insertion of distal cutting surface 84 into superior cortex 126. For example, the surgeon may decide to advance the cutting surface a desired depth into the superior cortex. For example, the desired depth may be approximately 1 mm or 1.5 mm (or another depth between 1 and 1.5 mm, inclusive). (The superior cortex generally has a thickness of 0.5 to 1.5 mm.)

Generally, upon the conclusion of this step of the procedure, a residual portion 146 of superior cortex 126 remains between distal-most portion 96 of cutting protrusion 82 and Schneiderian membrane 144. Residual portion 146 typically has a thickness of no more than 1 mm. Alternatively, cortex drill 50 sometimes cuts completely through superior cortex 126 (not shown). In either case, the surgeon withdraws cortex drill 50 from alveolar ridge 120.

Cutting with cortex drill 50 weakens the superior cortex sufficiently to enable a dental implement to readily break through the remaining portion of the superior cortex, as described hereinbelow with reference to FIG. 4F-H. Without this weakening, it is sometimes difficult to achieve sufficient mechanical support from trabecular bone 134 or relatively thin occlusal cortex 132 to enable a tool or implant to engage laterally with the osteotomy with sufficient traction to press forward against the cortex with sufficient force to cut through the hard superior cortical bone. As described hereinbelow with reference to FIGS. 4F-H, the implement subsequently is placed in and engages the perimeter of this bore, gaining traction that assists in breaking the residual bone. In addition, the implement (typically a screw thread thereof, or a distal tip thereof with a cylindrical or conical outer contour) forms a tight liquid seal with the perimeter of the bore, which facilitates the subsequent injection of fluids to the sub-membrane space without leakage into the trabecular bone or out back through the osteotomy.

Alternatively, at the step described with reference to FIG. 4E, cortex drill 60 is used, such as described hereinbelow with reference to FIGS. 6A-B, 6C, and/or 6D.

If cortex drill 50 did not cut completely through superior cortex 126, the surgeon cuts through (e.g., cracks through) the superior cortex, using a dental implement other than cortex drill 50. For some applications, the dental implement is a dental implant 150, such as shown in FIGS. 4F-H and 5A. For example, dental implant 150 may comprise one of the dental implants described in PCT Publication WO 2010/035270, PCT Publication WO 2010/146573, US Patent Application Publication 2010/0255446, U.S. Pat. No. 7,934,929, and/or U.S. Pat. No. 8,029,284 (collectively referred to hereinbelow as the "Assignee Publications"), all of which are assigned to the assignee of the present application and are incorporated herein by reference. For example, for applications in which the dental implement comprises a dental implant, the implant may have a diameter of between 2.5 and 7.0 mm, such as 3.7 mm, 4.2 mm, or 5.0 mm, depending on the diameter of the osteotomy.

As shown in FIG. 4F, the surgeon advances the dental implant into the preparatory osteotomy, such as by rotating the dental implant, until the distal end of the dental implant reaches residual portion 146 of superior cortex 126, as shown in FIG. 4G. As shown in FIG. 4H, the surgeon uses the dental implant to cut through (e.g., crack, as shown in FIG. 4H) the remaining portion of superior cortex 126, such as by rotating the dental implant. For some applications, the dental implant is rotated using techniques and/or tools described in one or more of the Assignee Publications. Typically, the distal end of dental implant 150 is shaped so as to define a cutting surface (e.g., a milling surface), which is used to cut through the superior cortex. The milling surface generally pushes bone forward into the Schneiderian membrane. As a result, any sharp surface that may be defined by the edge of flat distal cutting surface 84 is unlikely to damage the Schneiderian membrane.

Alternatively or additionally, an external lateral surface of dental implant 150 is shaped so as to define a screw thread, which extends until the distal end of the implant. The screw thread helps advance the implant distally through the remaining cortical bone, engaging the perimeter of the bore formed in the residual bone of the cortex. In addition, the screw thread forms a tight liquid seal with the perimeter of the bore, which facilitates the subsequent injection of fluids to the sub-membrane space without leakage into the trabecular bone or out back through the osteotomy.

Alternatively, the dental implement is a dental tool, such as a dental osteotome (for example, as shown in and described hereinbelow with reference to FIG. 5B), which is used to cut through, e.g., crack or fracture, the remaining portion of superior cortex 126. An external surface of the dental tool may be shaped so as to define a screw thread, and/or may be configured to be rotated in the osteotomy. For some applications, the dental tool has all or a portion of the features of the dental drills shown in and described in FIG. 14 and/or FIG. 20 of U.S. Pat. No. 8,029,284, which is assigned to the assignee of the present application and incorporated herein by reference. For applications in which the dental osteotome is as described hereinbelow with reference to FIG. 5B, a screw thread extends until the distal end of the osteotome. The screw thread helps advance the implant distally through the remaining cortical bone, engaging the perimeter of the bore formed in the residual bone of the cortex. In addition, the screw thread forms a tight liquid seal with the perimeter of the bore, which facilitates the subsequent injection of fluids to the sub-membrane space without leakage into the trabecular bone or out back through the osteotomy.

If cortex drill 50 cut completely through superior cortex 126 at the steps described hereinabove with reference to FIG. 4E, it is not necessary to use a dental implant or dental tool to cut through the superior cortex.

For applications in which dental implant 150 is shaped so as to define a lumen therethrough that opens through a distal external surface, such as described in the Assignee Publications, the implant procedure continues as described with reference to FIGS. 4I-N. For some applications, the dental implement comprises the dental osteotome shown in and described with reference to FIGS. 24A-C and 25 of U.S. Pat. No. 8,029,284. For these applications, the implant procedure continues as described hereinbelow with reference to FIGS. 4F-H and 4K-L, mutatis mutandis, using the osteotome instead of the implant.

As shown in FIG. 4I, the surgeon attaches an applicator 160 to a proximal end of dental implant 150, such as using techniques described in one or more of the Assignee Publications. Alternatively, applicator 160 is attached to the dental implant prior to beginning the procedure. The surgeon couples a retaining assembly 162 to applicator 160, and deploys the retaining assembly such that retaining assembly 162 sealingly couples a delivery tube 170 to a lateral opening 172 of the implant, as shown in FIG. 4J. For some applications, a sealing element at the distal end of delivery tube is configured as described hereinbelow with reference to FIG. 12. Lateral opening 172 of the implant is in fluid communication with the implant lumen that leads to the distal external surface of the implant, as described in the Assignee Publications. The distal end of delivery tube 170 may be held tightly against lateral opening 172 by tightening a knob 174 such that a screw 176 connected to the knob presses against applicator 160.

As shown in FIG. 4K, the surgeon gently lifts and separates membrane 144 from the top of maxillary ridge 120 into a maxillary sinus 180. In order to do so, the surgeon injects a fluid 182 from a fluid source (not shown), such as via a fluid connector 184 (e.g., a female luer connector), via delivery tube 170 and the lumen of implant 150, so as to form a cavity in maxillary sinus 180 under the membrane between the ridge and the membrane. Typically, fluid 182 is a biocompatible solution such as normal saline solution or a gas. Typically, the surgeon injects sufficient fluid 182 into cavity 180 to inflate the cavity to a vertical height of between about 2 and about 20 mm from the top of ridge 120, such as between about 2 and about 11 mm, e.g., between about 2 and about 8 mm. For some applications, a measured volume of fluid 182 is injected in order to achieve the desired cavity height, such as between about 0.5 and about 6 ml of fluid, e.g., between about 1 and about 4 ml, or between about 2 and about 4 ml. It is noted that the thread of the implant engages the dense cortical bone, forming a tight liquid seal with the bone, while vertical slots of the implant typically fill with compacted bone dust, maintaining this tight liquid seal with the bone.

The fluid is typically drained from the cavity, and the surgeon injects a regenerative material 186, such as liquid or gel bone graft, into cavity 180. The fluid source or a separate syringe or powered drug delivery device is used for injecting the regenerative material. Regenerative material 186 may comprise an allograph, an autogeneous bone graft, or a xenograft, and may, for example, comprise a natural material, a synthetic material, or a mixture thereof. For example, regenerative material 130 may comprise one of the following commercially available fluid bone graft materials: MBCP Gel (Biomatlante), DBX Paste (MTF), Allomatrix (Wright), Cerament (Bone Support), DynaGraft (Citagenix/ISOTIS), Fisiograft (Ghimas), Grafton (Osteotech), Optium DBM Gel (Lifenet/Depuy J&J), OsteoMax (Orthfix), PD VitalOs Cemen (VitalOs), Regenafil® (Exactech), or fluids containing an active biological ingredient such as bone morphogenetic protein.

Alternatively, the surgeon injects regenerative material 186, rather than fluid 182, to lift membrane 144, thereby combining two steps of the procedure described above. In this case, the regenerative material typically comprises a liquid.

The surgeon decouples delivery tube 170 from implant 150, and retaining assembly 162 from applicator 160, as shown in FIG. 4L.

Figure 4M:
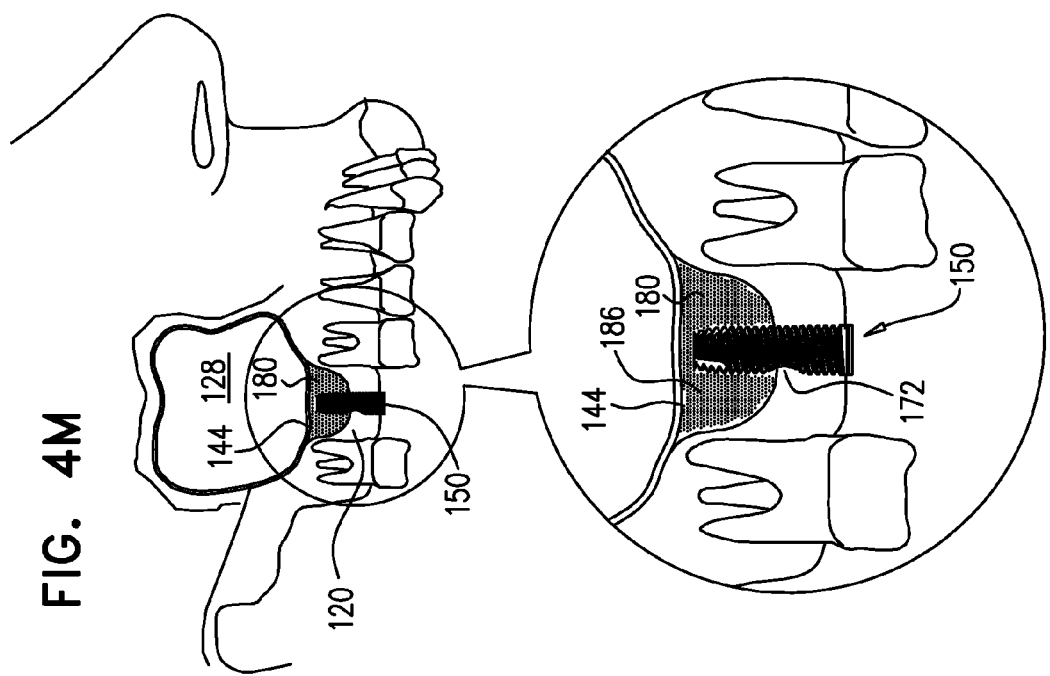

The surgeon further advances (e.g., by rotating or screwing) implant 150 into regenerative material 186 in cavity 180, and detaches applicator 160 from implant 150, as shown in FIG. 4M. For some applications, techniques are used that are described in the Assignee Publications. Implant 150 is advanced at least until lateral opening 172 of the implant is positioned entirely within the bore in ridge 120 and/or in regenerative material 186 in cavity 180. Such positioning of both ends of the lumen of the implant within bone substantially reduces the risk of infection, because the proximal end of the implant that is exposed to the oral cavity or gingiva is permanently closed. Typically, the surgeon couples a cover screw to the proximal end of the implant using a hand driver, and sutures the gingiva.

As shown in FIG. 4N, after bone grows into regenerative material 186 and is integrated into ridge 120, an appliance 190, such as a crown, is coupled to implant 150, typically using an abutment 192 coupled to implant 150, as is known in the art. Alternatively, implant 150 comprises a single-stage transgingival implant/abutment, as is known in the art.

Figure 5A:
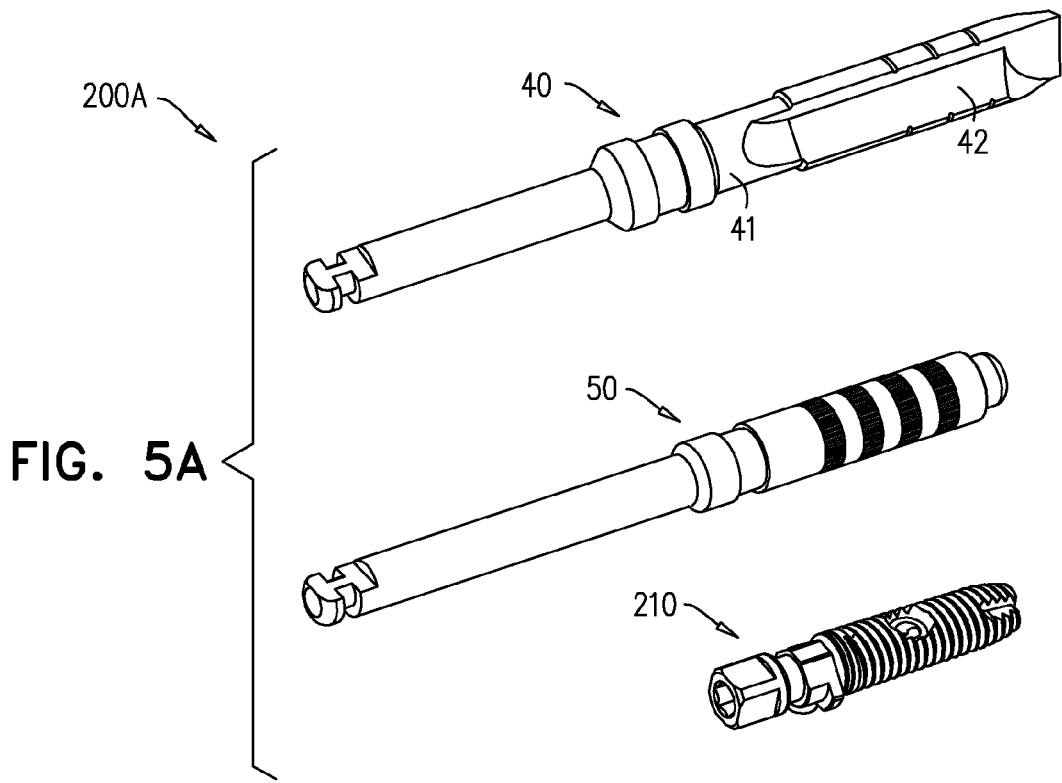
FIGS. 5A and 5B are schematic illustrations of dental surgical kits, respectively, in accordance with respective applications of the present invention.
Figure 5B:
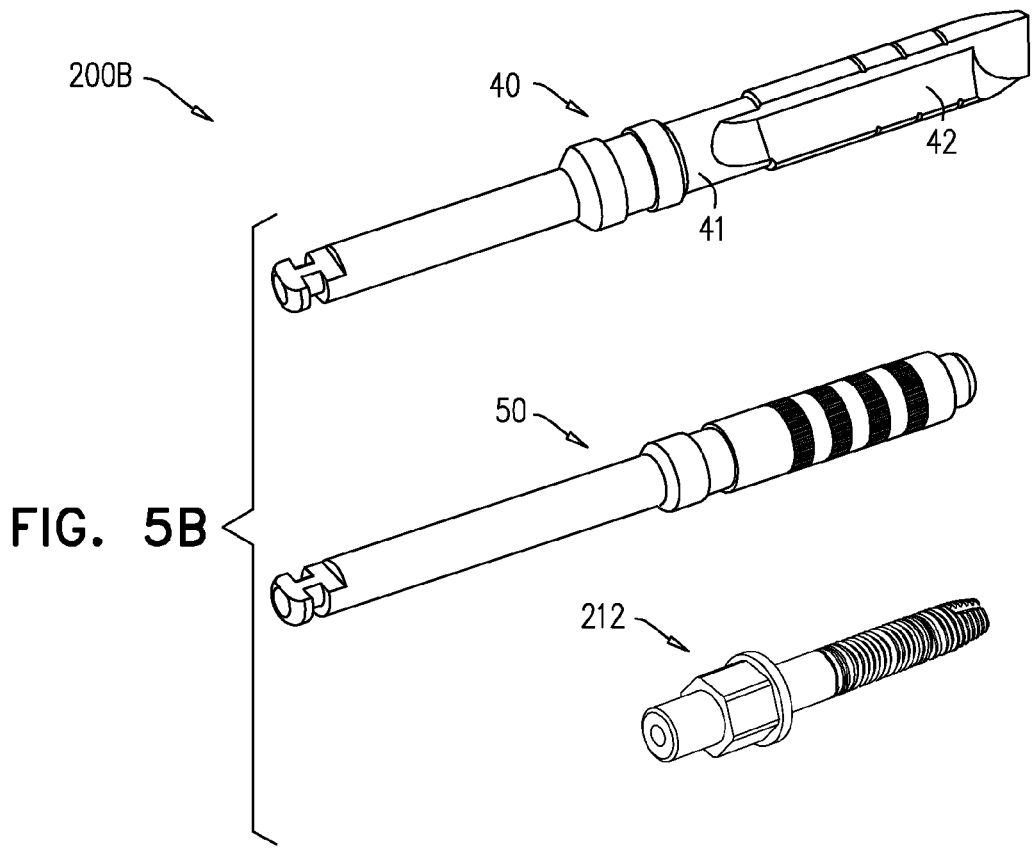

Reference is made to FIGS. 5A and 5B, which are schematic illustrations of dental surgical kits 200A and 200B, respectively, in accordance with respective applications of the present invention. Each of kits 200A and 200B comprises at least one flat drill 40, which, as described hereinabove, is shaped so as to define shaft 41 and flat distal cutting edge 42. Optionally, each of the kits comprises a plurality of flat drills 40 having different respective diameters. In addition, each of kits 200A and 200B comprises at least one cortex drill. Optionally, each of the kits comprises a plurality of cortex drills having different respective diameters. For some applications, as shown in FIGS. 5A and 5B, the at least one cortex drill comprises cortex drill 50, described hereinabove with reference to FIGS. 2 and 3A-B. Alternatively, for some applications, the at least one cortex drill is not shaped so as to define shoulder 90. Further alternatively, for some applications, the at least one cortex drill comprises cortex drill 60, described hereinbelow with reference to 6A-B, 6C, and/or 6D. For some applications, a diameter of flat drill 40 is within +/−100 of the diameter of the portion of shaft 41 of the cortex drill that is proximally adjacent the distal cutting surface of the cortex drill. For some applications, the at least one cortex drill comprises at least one cortex drill 50 and at least one cortex drill 60, which may provide the surgeon the flexibility of selecting the most appropriate type of cortex drill during a surgical procedure.

Each of kits 200A and 200B further comprises at least one dental implement, which is shaped so as to define a cutting surface at a distal end thereof. Optionally, each of the kits comprises a plurality of dental implements, having different respective dimensions, such as different respective diameters and/or lengths. Typically, the at least one dental implement comprises a dental implant or a dental osteotome. Optionally, a single kit comprises both at least one dental implant and at least one dental osteotome. As shown in FIG. 5A, kit 200A further comprises a dental implant 210. For some applications, dental implant 210 comprises one of the dental implants described in the Assignee Publications. Optionally, a screw thread of implant 210 extends until the distal end of the implant. As shown in FIG. 5B, kit 200B further comprises a dental osteotome 212. For some applications, dental osteotome 212 comprises the dental osteotome shown in and described with reference to FIGS. 24A-C and 25 of U.S. Pat. No. 8,029,284. Optionally, a screw thread of osteotome 212 extends until the distal end of the osteotome.

Optionally, each of kits 200A and 200B further comprises additional dental tools, such as additional dental drills. For example, the kits may comprise one or more pilot drills 20 (optionally, having different respective diameters) and/or one or more counterbore drills 30 (optionally, having different respective diameters), such as described hereinabove with reference to FIG. 1.

For some applications in which osteotome 212 is used to cut through the superior cortex (such as described hereinabove with reference to FIGS. 4F), the surgeon introduces a tool through the channel of the osteotome, and uses the tool to complete the fracture of the cortex. For example, the tool may be another dental implement, such as a drill or chisel, or an ultrasound transducer (e.g., a microtransducer). Alternatively or additionally, the osteotome may comprise an ultrasound transducer, e.g., a microtransducer, near the distal end of the osteotome. The technique described in the present paragraph may be used in combination with the techniques described hereinabove with reference to FIGS. 4A-N, with only a portion of these techniques, or separately from these techniques.

Reference is made to FIGS. 6A-D, which are schematic illustrations of several alternative techniques for weakening superior cortex 126, in accordance with respective applications of the present invention. These techniques may be used instead of the cortex weakening techniques described hereinabove with reference to FIG. 4E, and are typically performed as part of an implantation procedure including some or all of the other steps of the procedure described hereinabove with reference to FIGS. 4A-N.

Figure 6A:
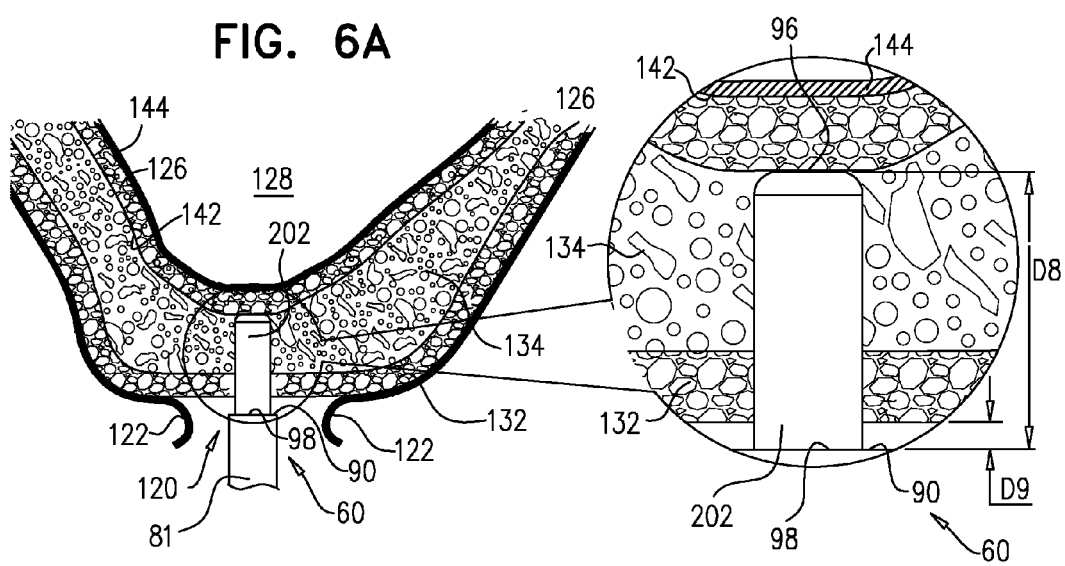
FIGS. 6A-D are schematic illustrations of several alternative techniques for a weakening superior cortex, in accordance with respective applications of the present invention.

In the application shown in FIG. 6A, cortex drill 60 is used to weaken superior cortex 126. Cortex drill 60 is similar to cortex drill 50, described hereinabove with reference to FIGS. 2 and 3A-B, except that a cutting protrusion 202 of cortex drill 60 is substantially longer than cutting protrusion 82 of cortex drill 50. Typically, distal-most portion 96 of cutting protrusion 202 extends a distance D8 of at least 4 mm, such as at least 8 mm, distally beyond distal end 98 of shaft 81, and/or no more than 15 mm distally beyond distal end 98 of shaft 81.

Cortex drill 60 is sized such that shoulder 90 thereof comes in contact with the occlusal surface of occlusal cortex 132

(instead of the occlusal surface of superior cortex 126, as in the case of cortex drill 50). Such contact prevents further advancement of cortex drill 60. The distance from the occlusal surface of occlusal cortex 132 to Schneiderian membrane 144 varies substantially from patient to patient. In order to assess this distance, the surgeon advances cortex drill 60 into the preparatory osteotomy until the distal end of cutting protrusion 202 reaches the occlusal surface of superior cortex 126 (at the interface with trabecular bone 134). The surgeon can typically manually sense the interface. With the drill thus positioned, the surgeon measures a distance D9 between the distal surface of shoulder 90 and the occlusal surface of occlusal cortex 132. Optionally, the lateral surface of cutting protrusion 202 is marked as a ruler to aid in this measurement. Alternatively, the depth of the osteotomy may be measured using a depth guide (either visually or with the assistance of a radiograph).

If, as shown in FIG. 6A, distance D9 is approximately equal to an estimated thickness of occlusal cortex 132 (e.g., is approximately 1.5 mm), the surgeon advances cortex drill 60 and cuts into occlusal cortex 132, as described hereinabove with reference to FIG. 4E. The distal surface of shoulder 90 comes in contact with the occlusal surface of occlusal cortex 132 at the same moment as the distal end of cutting protrusion 202 advances sufficiently (e.g., 1.5 mm) into superior cortex 126.

Figure 6B:
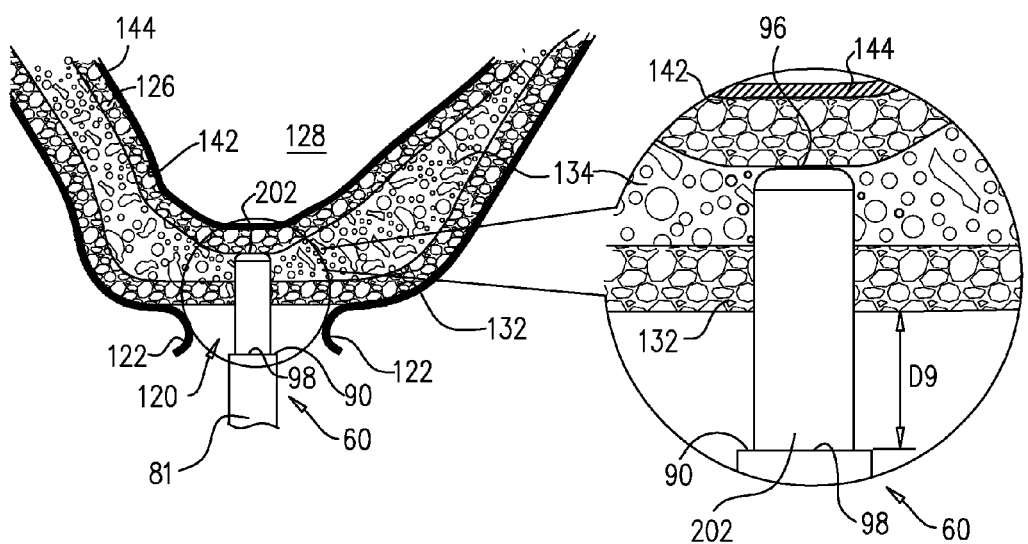

On the other hand, if, as shown in FIG. 6B, distance D9 is greater than the estimated thickness of occlusal cortex 132 (e.g., is greater than 1.5 mm), the surgeon removes cortex drill 60 from the preparatory osteotomy, and inserts another cortex drill 60 that has a cutting protrusion having an appropriate length. For example, if the measured distance were approximately 2.5 mm, the surgeon would use another cortex drill with a cutting protrusion having a length that is approximately 1 mm shorter than the length of the cutting protrusion of the first cortex drill. Thus, for this application, a kit is provided having a plurality of cortex drills having cutting protrusions having respective different lengths.

Figure 6C:
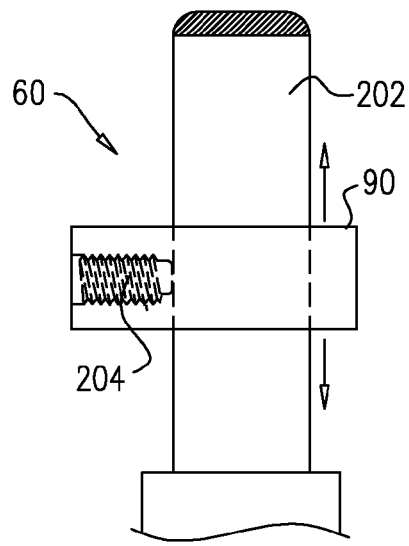

Alternatively, as shown in FIG. 6C, shoulder 90 is slidable with respect to cutting protrusion 202 along cortex drill 60. For example, cortex drill 60 may comprise a set screw 204 in the side of the drill or the shoulder, which fixes the shoulder at a desired distance from the distal end of cutting protrusion 202. The surgeon slides the shoulder to set distance D9 at approximately the estimated thickness of occlusal cortex 132 (e.g., approximately 1.5 mm), and locks the shoulder in place before cutting into superior cortex 126.

Figure 6D:
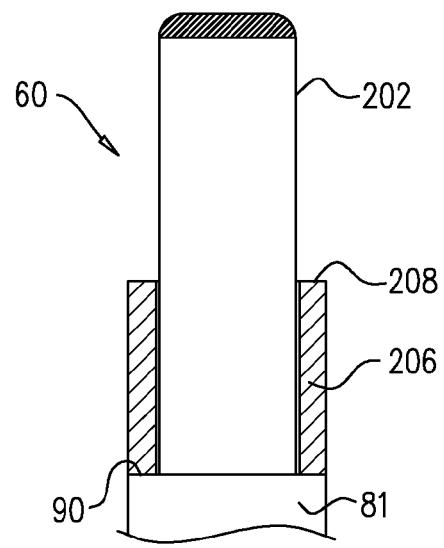

Further alternatively, as shown in FIG. 6D, cortex drill 60 comprises a plurality of cylindrical skirts 206 (only a single one of the skirts is shown in FIG. 6D), having a plurality of respective different longitudinal lengths. Each of the skirts is shaped so as to define a lumen that is sized to pass over cutting protrusion 202, and rest against shoulder 90, thus effectively creating a distally-augmented shoulder 208 at a distal end of the skirt. The skirt thus reduces the effective length of cutting protrusion 202 by the length of the skirt. A skirt is selected that has a length approximately equal to the difference between distance D9 and the estimated thickness of occlusal cortex 132.

Reference is now made to FIGS. 7A-B, which are schematic illustrations of a dental system 300 and a method for its use, in accordance with an application of the present invention. Dental system 300 is used for performing a stent-assisted sinus lift procedure, and comprises a surgical guide stent 310 and a dental implement 312. Dental system 300 allows the screwing of dental implement 312 into an osteotomy, and removal of the implement from the osteotomy, without damaging the internal wall of the osteotomy or occlusal cortex 132.

Surgical guide stent 310 has proximal and distal surfaces 314 and 316, and is shaped so as to define a frame 317 that defines an opening 318. Surgical guide stent 310 comprises a support element 320, which is shaped so as to define a cylindrical inner surface 322, which is aligned with opening 318 and extends proximally away from the opening. Cylindrical surface 322 is shaped so as to define an internal thread 324. For some applications, support element 320 is integrated with frame 317, while for other applications, support element 320 is coupled to frame 317 during the surgical procedure. For some applications, surgical guide stent 310 is customized for each individual patient's alveolar ridge, for example, such that the surgical stent guide fits the external contour of the gingiva; at least frame 317 is custom-fabricated to fit the patient's anatomy and the surgical plan for the patient, using custom fabrication techniques known in the art. For some applications, surgical guide stent 310 comprises plastic.

Optionally, dental system 300 further comprises a plurality of fixation elements 326, such as screws, which are configured to couple surgical guide stent 310 to the occlusal surface of occlusal cortex 132 (or to the gingiva). For some applications, the fixation elements are configured to penetrate the gingiva into the bone. Alternatively, for other applications, the fixation elements are configured to be affixed to (e.g., cover) adjacent teeth.

Dental implement 312 has an outer surface 330, a portion of which is shaped so as to define an external thread 332 that is configured to engage internal thread 324 of cylindrical surface 322 of support element 320. Dental implement 312 has a distal end 334 that is shaped so as to define a cutting surface 336. For some applications, a distal end 338 of external thread 332 of dental implement 312 is at least a distance D10 of 8 mm from distal end 334 of dental implement 312. For other applications, external thread 332 extends distally closer to distal end 334 of dental implement 312, such as to the distal end of the dental implement. For these applications, the diameter of the dental implement is typically less than the diameter of osteotomy 350, so that the thread does not engage the inner wall of the osteotomy.

For some applications, dental implement 312 comprises a dental osteotome, dental drill, or other dental tool. Typically, dental implement 312 comprises a handle 340, as shown, or an interface to another tool, such as a ratchet wrench (configuration not shown).

Reference is still made to FIGS. 7A-B. During a procedure using dental system 300, the surgeon couples support element 320 to the occlusal surface of alveolar ridge 120, such that support element 320 extends proximally away from alveolar ridge 120, as shown in FIG. 7A. For some applications, the surgeon couples the support element to the occlusal surface using surgical guide stent 310 (for example, such that the surgical stent guide fits the external contour of the gingiva). For other applications, the support element is otherwise coupled to the occlusal surface, in which the remainder of surgical guide stent 310 is not provided. For some applications, the surgeon couples the surgical guide stent to the occlusal surface by inserting fixation elements 326 into respective osteotomies in occlusal cortex 132 at respective locations, each of which is at least a minimum distance, e.g., 3 mm, from a center of a site of the osteotomy. For some applications, the surgeon couples support element 320 to the occlusal surface of alveolar ridge 120 through gingiva covering the occlusal cortex. Alternatively, for other applications, support element 320 is configured to be affixed to (e.g., cover) adjacent teeth. Alternatively, the surgeon reflects gingiva covering the alveolar ridge, and thereafter couples support element 320 to the exposed occlusal surface of the alveolar ridge.

Before or after coupling support element 320 to the occlusal surface, the surgeon forms, using a cutting tool (not shown), an osteotomy 350 through occlusal cortex 132 into trabecular bone 134 of alveolar ridge 120 toward a maxillary sinus, without reaching Schneiderian membrane 144. The surgeon typically does not intentionally cut into superior cortex 126 at this stage of the implantation procedure, although such cutting may occur inadvertently. For some applications, the surgeon ceases drilling at (a) a predetermined distance short of sinus 128, or (b) at the trabecular-cortical bone interface.

As shown in FIG. 7B, after coupling support element 320 to the occlusal surface, the surgeon engages, with internal thread 324 of cylindrical inner surface 322 of the support element 320, external thread 332 defined by outer surface 330 of a portion of dental implement 312 (other than the cutting tool). While dental implement 312 is engaged with cylindrical surface 322, the surgeon rotates dental implement 312 such that the dental implement advances into osteotomy 350. The surgeon cuts, e.g., breaks, superior cortex 126 of alveolar ridge 120 using dental implement 312. Support element 320, rather than occlusal cortex 132 and trabecular bone 134, provides most of the mechanical support for the rotation of dental implement 312. As a result, the rotation of dental implement does not weaken the occlusal cortex or trabecular bone. Optionally, support element 320 may additionally provide guidance for the dental implement. Optionally, the surgeon uses dental implement 132 to elevate the Schneiderian membrane and/or to insert a regenerative material into a cavity formed under the Schneiderian membrane, such as described hereinabove and/or in the Assignee Publications.

The surgeon removes the dental implement from the osteotomy and decouples support element 320 from the occlusal surface of occlusal cortex 132 or the gingiva (steps not shown). Optionally, the surgeon inserts a dental implant into the completed osteotomy. For applications in which the dental implant is shaped so as to define a lumen therethrough that opens through a distal external surface, such as described hereinabove and/or in the Assignee Publications, the implant procedure continues as described hereinabove with reference to FIGS. 4I-N.

For some applications, after forming the osteotomy and before breaking superior cortex 126 using dental implement 312, the surgeon weakens superior cortex 126 using cortex drill 50, using the techniques described hereinabove with reference to FIG. 4E.

For some applications, the techniques described above with reference to FIGS. 7A-B are used for performing a crestal sinus lift. Alternatively, these techniques may be used for performing a lateral sinus lift, such as if a prosthesis is already in place before the procedure.

Reference is made to FIG. 8, which is a schematic illustration of another configuration of dental implement 312, in accordance with an application of the present invention. In this configuration, dental implement 312 comprises a tool 360 and a dental implant 362. A proximal end of dental implant 362 is removably coupled to a distal end of tool 360. An outer surface of a portion of tool 360 serves at the portion of outer surface 330 of dental implement 312 that defines external thread 332. Dental implant 362 is shaped so as to define cutting surface 336 of dental implement 312 at a distal end of dental implant 362.

During the procedure, the surgeon engages external thread 332 (defined by the outer surface of the portion of tool 360) with internal thread 324 (defined by cylindrical inner surface 322 of support element 320), while the proximal end of dental implant 362 is removably coupled to the distal end of tool 360. The surgeon uses dental implant 362 to break superior cortex 126. After breaking superior cortex 126, the surgeon decouples tool 360 from dental implant 362, and withdraws tool 360 from osteotomy 350, leaving dental implant 362 in the osteotomy.

For some applications, dental implement 312 further comprises an internal screw 370. Internal screw 370, tool 360, and dental implant 362 are configured such that the internal screw passes through tool 360 and removably couples the tool to the proximal end of dental implant 362. A proximal end of screw 370 is accessible from a proximal end of tool 360 when the tool is coupled to the dental implant. The surgeon unscrews screw 370 from dental implant 362 in order to decouple tool 360 from dental implant 362.

Figure 9A:
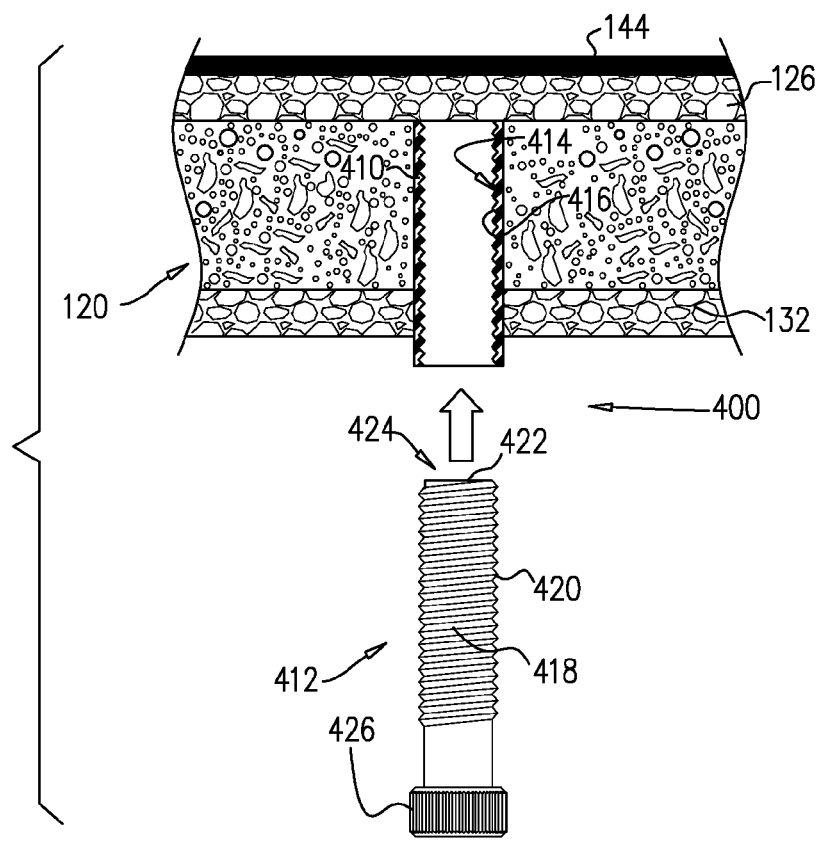
FIGS. 9A-B are schematic illustrations of yet another dental system and a method for its use, in accordance with an application of the present invention.
Figure 9B:
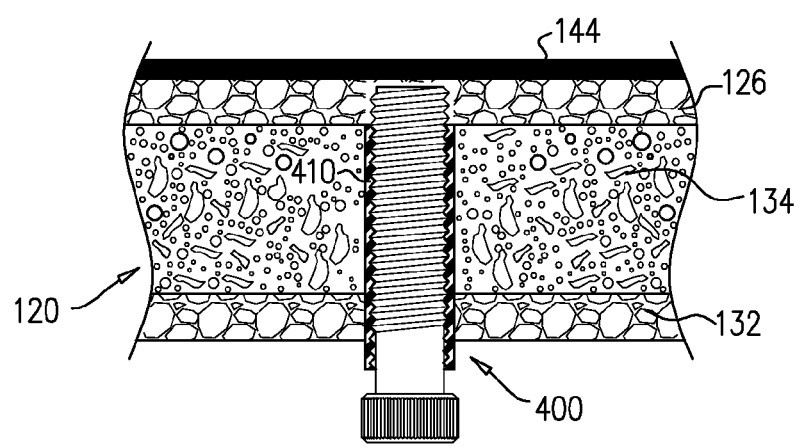

Reference is now made to FIGS. 9A-B, which are schematic illustrations of a dental system 400 and a method for its use, in accordance with an application of the present invention. Dental system 400 comprises an osteotomy sheath 410 and an osteotome 412. An inner surface 414 of sheath 410 is shaped so as to define an internal thread 416. Osteotome 412 is shaped so as to define a shaft 418 having an external thread 420, and a cutting surface 422, such as a cracking tip, at a distal end 424 of the osteotome. Typically, osteotome 412 comprises a handle 426, as shown, or an interface to another tool, such as a ratchet wrench (configuration not shown).

External and internal threads 420 and 416 are shaped and sized such to engage each another when osteotome 412 is rotated inside sheath 410. Typically, the external and internal threads share a common thread pitch.

For some applications, sheath 410 comprises rubber. For other applications, sheath 410 comprises a metal; optionally, sheath 410 further comprises a rubber coating that coats at least a portion of an external surface of the metal. For some applications, sheath 410 has an inner diameter of at least 1 mm, no more than 5 mm, and/or between 1 and 5 mm, and/or a length of at least 2 mm, no more than 8 mm, and/or between 2 and 8 mm.

Reference is still made to FIGS. 9A-B. During a procedure using dental system 400, the surgeon forms an osteotomy 430 in alveolar ridge 120 through occlusal cortex 132 into trabecular bone 134. The surgeon may form the osteotomy (a) through trabecular bone 134 up to, but not into, superior cortex 126, (b) through trabecular bone 134 without reaching superior cortex 126, or (c) through trabecular bone 134 and partially through superior cortex 126. Optionally, the surgeon forms the osteotomy using techniques described hereinabove with reference to FIGS. 1 and/or 4A-D. As shown in FIG. 9A, the surgeon introduces osteotomy sheath 410 into osteotomy 430.

As shown in FIG. 9B, the surgeon introduces osteotome 412 into sheath 410 in osteotomy 430. The surgeon rotates osteotome 412 in sheath 410 in osteotomy 430 such that external thread 420 engages internal thread 416 and osteotome 412 advances distally in sheath 410 at least until cutting surface 422 cuts into superior cortex 126 of alveolar ridge 120. The surgeon removes osteotome 412 and sheath 410 from osteotomy 430 (step not shown).

The rotating engagement of internal and external threads 416 and 420 with each other prevents rotation of sheath 410 with respect to osteotomy 430, while still allowing osteotome 412 to engage the inner wall of osteotomy 430. Because external thread 420 of osteotome 412 does not directly engage or otherwise come in contact with the bone of the wall of osteotomy 430, the thread does not damage the bone. The sheath is pressed outwardly so that it grips the osteotomy and prevents rotation or vertical movement with respect to the osteotomy. In addition, the sheath may prevent leakage of liquid injected during the subsequent stages of the procedure.

For some applications, after forming osteotomy 430 and before breaking superior cortex 126 using osteotome 412 (before or after inserting sheath 410 into the osteotomy), the surgeon weakens superior cortex 126 using cortex drill 50, using the techniques described hereinabove with reference to FIG. 4E.

Figure 10A:
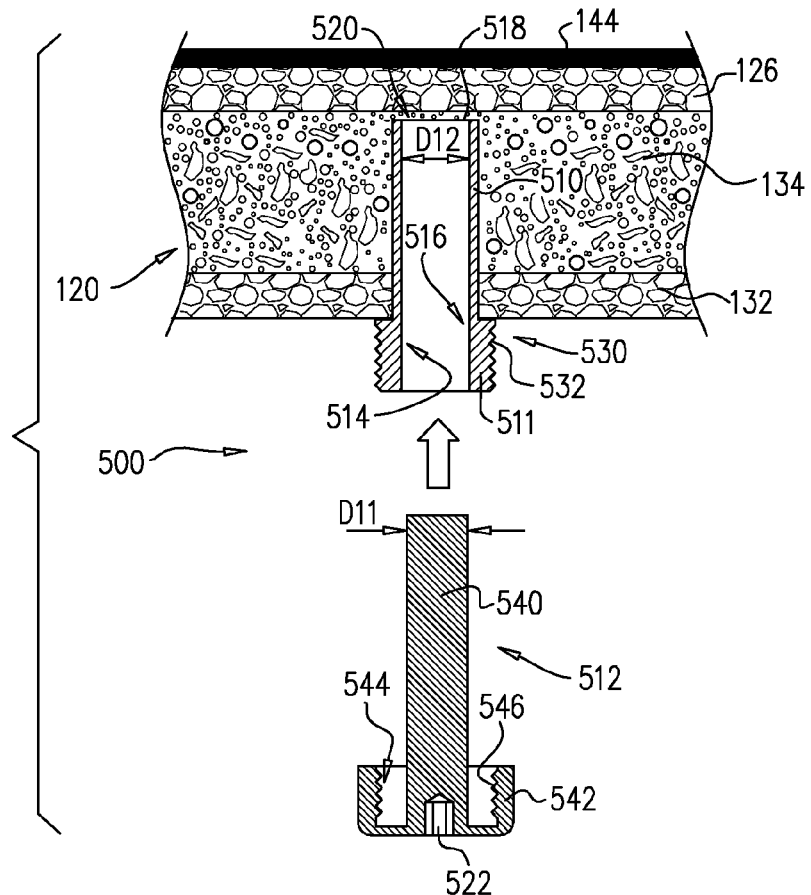
FIGS. 10A-B are schematic illustrations of still another dental system and a method for its use, in accordance with an application of the present invention.
Figure 10B:
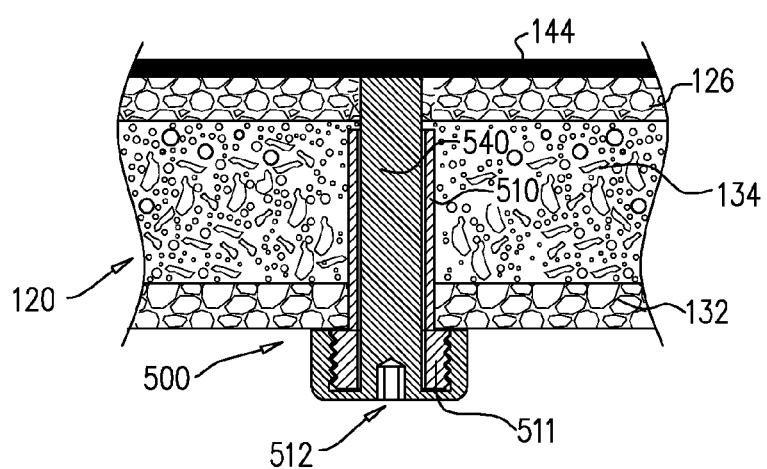

Reference is now made to FIGS. 10A-B, which are schematic illustrations of a dental system 500 and a method for its use, in accordance with an application of the present invention. Dental system 500 comprises an osteotomy sheath 510, an external support element 511, and an osteotome 512. External support element 511 is shaped so as to define a cylindrical inner surface 514. A proximal portion 516 of sheath 510 is fixed to external support element 511, such that proximal portion 516 cannot rotate with respect to external support element 511. For example, proximal portion 516 may be fixed to cylindrical inner surface 514, as shown in FIG. 10A. Osteotome 512 is shaped so as to define a cutting surface 518, such as a cracking tip, at a distal end 520 thereof. Typically, a shaft 540 of osteotome 512 has an outer diameter D11 that is between 50% and 100% of an inner diameter D12 of sheath 510. Typically, a proximal end of osteotome 512 is shaped so as to define a coupling surface 522, such as a male surface or a female socket, e.g., a male or female hexagonal surface. An external tool, such as a ratchet wrench, can be coupled to the surface for rotating the osteotome.

For some applications, as shown in FIGS. 10A-B, external support element 511 is shaped so as to define a cylindrical outer surface 530, which is shaped so as to define an external thread 532. For these applications, osteotome 512 typically is shaped so as to define shaft 540 and a coupling element 542 fixed to a proximal portion of the shaft. Coupling element 542 is shaped so as to define a cylindrical inner surface 544, which is shaped so as to define an internal thread 546. Internal thread 546 is configured to engage external thread 532 of external support element 511.

For other applications, an inner surface of at least part of proximal portion 516 of sheath 510 is shaped so as to define an internal thread, similar to internal thread 416 in the configuration described hereinabove with reference to FIGS. 9A-B. The shaft of the osteotome presses against the sheath, causing the sheath to press outwardly such that the sheath grips the osteotomy and prevents rotation or vertical movement with respect to the osteotomy. Alternatively or additionally, cylindrical inner surface 514 is shaped so as to define an internal thread. For these applications, osteotome 512 is shaped so as to define an external thread on a proximal portion of a shaft thereof, similar to external thread 420 in the configuration described hereinabove with reference to FIGS. 9A-B, except that the external thread is typically more proximally positioned in the present configuration.

For some applications, sheath 510 comprises rubber. For other applications, sheath 510 comprises a metal; optionally, sheath 510 further comprises a rubber coating that coats at least a portion of an external surface of the metal. For some applications, sheath 510 further comprises an O-ring, which is coupled to an external surface of the metal at a distal end of the sheath. For some applications, sheath 510 has an inner diameter of between 1 and 5 mm, and/or a length of between 2 and 8 mm.

Reference is still made to FIGS. 10A-B. During a procedure using dental system 400, the surgeon forms an osteotomy 530 in alveolar ridge 120 through occlusal cortex 132 into trabecular bone 134. The surgeon may form the osteotomy (a) through trabecular bone 134 up to, but not into, superior cortex 126, (b) through trabecular bone 134 without reaching superior cortex 126, or (c) through trabecular bone 134 and partially through superior cortex 126. Optionally, the surgeon forms the osteotomy using techniques described hereinabove with reference to FIGS. 1 and/or 4A-D. As shown in FIG. 10A, the surgeon positions osteotomy sheath 510 and external support element 511 such that sheath 510 is within osteotomy 530 and external support element 511 is outside the osteotomy pressed against the occlusal surface of occlusal cortex 132 (the gingiva is typically, but not necessarily, reflected).

As shown in FIG. 10B, the surgeon introduces osteotome 512 into sheath 510 in osteotomy 530. The surgeon advances osteotome 512 in sheath 510 in osteotomy 530, such as by rotating the osteotome, at least until cutting surface 518 cuts into superior cortex 126 of alveolar ridge 120. The surgeon removes osteotome 412 and sheath 410 from osteotomy 430 (step not shown).

For applications in which external support element 511 is shaped so as to define externally-threaded cylindrical outer surface 530 and osteotome 512 comprises internally-threaded coupling element 542, the surgeon advances osteotome 512 by engaging internal thread 546 of coupling element 542 with external thread 532 of cylindrical outer surface 530 of external support element 511.

For applications in which the inner surface of proximal portion 516 of sheath 510 defines and internal thread and osteotome 512 defines an external thread, the surgeon advances osteotome 512 in sheath 510 by engaging the external thread of the osteotome with the internal thread of the cylindrical inner surface.

Because osteotome 512 does not directly engage or otherwise come in contact with the bone of the wall of osteotomy 530, the osteotome does not damage the bone. In addition, the sheath may prevent leakage of subsequently injected fluids.

For some applications, after forming osteotomy 430 and before breaking superior cortex 126 using osteotome 412 (before or after inserting sheath 410 into the osteotomy), the surgeon weakens superior cortex 126 using cortex drill 50, using the techniques described hereinabove with reference to FIG. 4E.

Reference is now made to FIGS. 11A-D, which are schematic illustration of cortex sealing techniques, in accordance with respective applications of the present invention. These techniques minimize leakage into the trabecular bone of fluid injected through a dental implement 550 to raise Schneiderian membrane 144, for example as described hereinabove with reference to FIG. 4K and/or 4L. Typically, dental implement 550 is a dental tool or a dental implant (e.g., a conventional dental implant, or one of the dental implants described herein and/or in the Assignee Publications). Dental implement 550 defines a lumen 554 therethrough that is open through a distal opening 556 to a distal end 558 of the dental implement. Distal opening 556 is disposed on a distal portion of the implement that extends from distal end 558 along up to 50% of a longitudinal length of the implement, such as up to 30% of the length, up to 150 of the length, or up to 5% of the length. Lumen 554 is additionally open to a lateral opening or a proximal opening of the implement.

These techniques are typically used after creating an osteotomy that reaches at least to superior cortex 126, such as: (a) reaches occlusal surface 142 of superior cortex 126, (b) passes partially through superior cortex 126, and (c) or passes entirely through superior cortex 126. By way of example, these techniques are described hereinbelow for option (b); residual portion 146 of superior cortex 126 remains past the distal end of the osteotomy, such as described hereinabove with reference to FIG. 4E. Residual portion 146 is shown cracked, typically using a separate tool at an earlier stage of the procedure.

For some applications, as shown in FIGS. 11A-C, a sealing element 552 is provided for preventing fluid leakage between distal opening 556 of dental implement 550 and trabecular bone 134.

In the configuration shown in FIG. 11A, sealing element 552 is shaped as a ring that surrounds a distal portion of dental implement 550, which distal portion typically has a length along an axis of the implement of no more than 3 mm. Sealing element 552 thus seals laterally against the wall of the osteotomy, typically a portion of the wall within superior cortex 126. The sealing element has an outer diameter that is sized to fit snugly with the wall of the osteotomy. For some applications, a distal portion of dental implement 550 is recessed by approximately the thickness of sealing element 552, in order to accommodate the sealing element. As a result, the outer surface of the sealing element is flush with the more proximal outer surface of the dental implement, as shown in FIG. 11A. Alternatively, the dental implement is not recessed to accommodate the sealing element, and the outer surface of the sealing element thus has a diameter that is greater than the outer surface of the dental implement (configuration not shown).

In the configuration shown in FIG. 11B, sealing element 552 is shaped as an O-ring that is positioned on a distal surface of distal end 558 of dental implement 550. Sealing element 552 thus seals in a forward direction against the distal end of the osteotomy, which is typically within superior cortex 126.

In the configuration shown in FIG. 11C, sealing element 552 is shaped as a ring that protrudes distally beyond distal end 558 of dental implement 550. Sealing element 552 thus seals both laterally against the wall of the osteotomy (typically a portion of the wall within superior cortex 126) and in a forward direction against the distal end of the osteotomy (which may be within superior cortex 126).

For some applications, sealing element 552 is fixed to dental implement 550 prior to insertion of dental implement 550 in the osteotomy, typically during manufacture of the dental implement. Alternatively, the sealing element is initially not fixed to the dental implement. The surgeon inserts the sealing element into the osteotomy, positions the sealing element properly (such as in a portion of the osteotomy that is within superior cortex 126), and then inserts the dental implement into the osteotomy and brings the dental implement into contact with the sealing element.

For some applications, as shown in FIG. 11D, a dental implement 560 is shaped so as to define a screw thread 562 along a distal portion 564 of the dental implement. Typically, dental implement 560 is a dental tool or a dental implant (e.g., a conventional dental implant, or one of the dental implants described herein and/or in the Assignee Publications). Dental implement 560 defines lumen 554 therethrough that is open through distal opening 556 to distal end 558 of the dental implement. Typically, distal portion 564 reaches to within 2 mm of distal end 558, such as to the distal end, and has a length of no more than 4 mm. The screw thread provides good lateral sealing between distal portion 564 and the wall of the osteotomy, typically a portion of the wall within superior cortex 126. For some applications, to provide the good sealing, screw thread 562 is oversized for the diameter of the osteotomy. Alternatively or additionally, the screw thread comprises a conic thread. Optionally, the screw thread is a self-tapping screw thread.

For some applications, dental implement 560 is implemented in combination with the sealing techniques described with reference to FIGS. 11A, 11B, or 11C.

For some applications, cortex drill 50, described hereinabove with reference to FIGS. 2 and 3A-B, is used to create a specific geometry of the distal portion of the osteotomy, for tight fitting with sealing element 552, and/or with screw thread 562.

Figure 12:
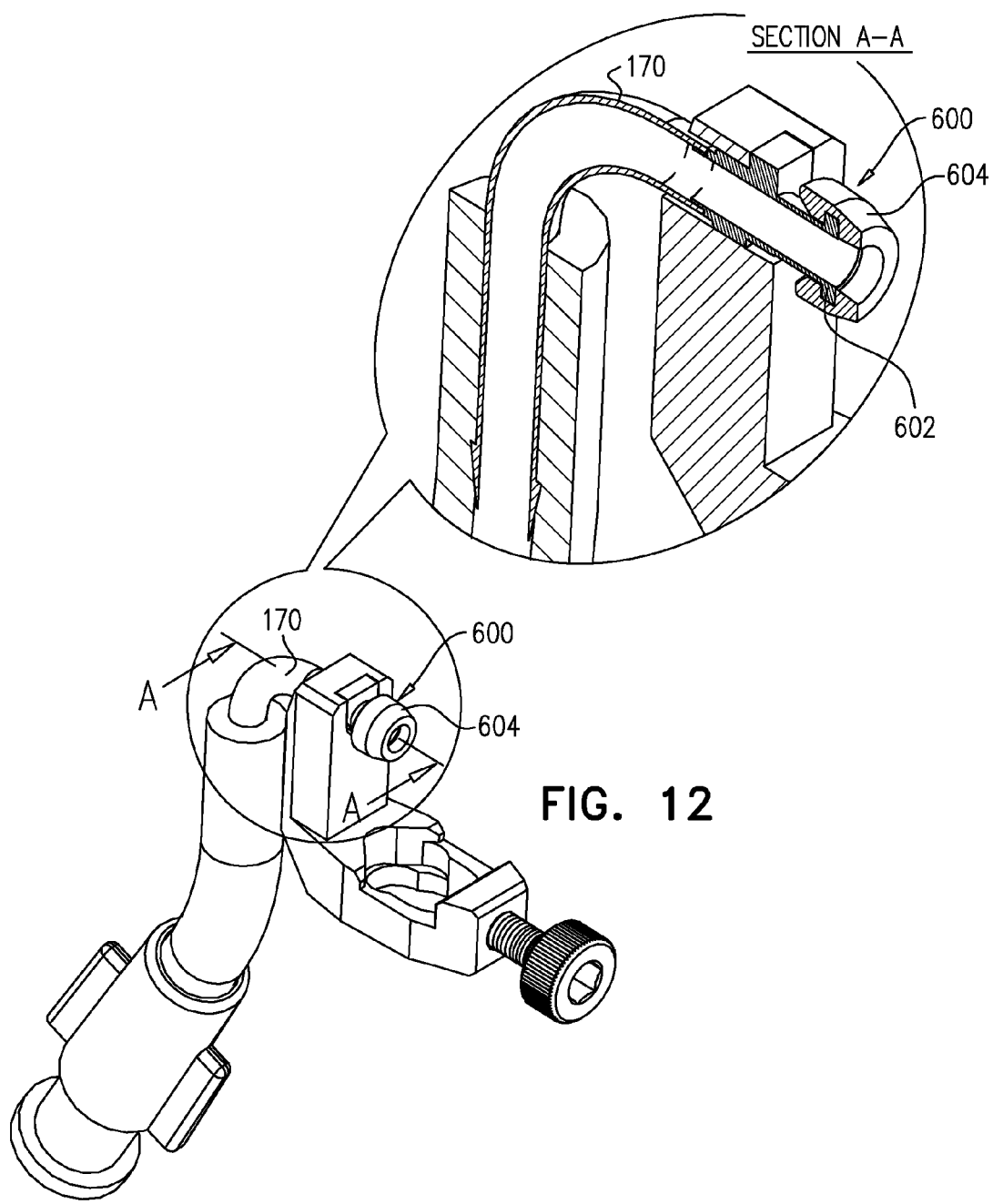
FIG. 12 is a schematic illustration of a configuration of a sealing element of a retaining assembly, in accordance with an application of the present invention.

Reference is now made to FIG. 12, which is a schematic illustration of a configuration of a sealing element 600 of retaining assembly 162, in accordance with an application of the present invention. In this configuration, retaining assembly 162 comprises sealing element 600 at the distal end of delivery tube 170. Typically, the distal end of delivery tube 170 is embedded in sealing element 600. Delivery tube 170 includes an increased-diameter distal portion 602, which may be disc-shaped, which helps couple tube 170 to sealing element 600, and forms a surface that applies even pressure to the sealing element, thereby helping the sealing element seal with lateral opening 172 of the implant. The sealing element may also be coupled to the tube using an adhesive. Sealing element 600 typically comprises silicone, silicone rubber, or another biocompatible compliant sealing material. For some applications, a distal portion 604 of sealing element 600 is conical. For example, distal portion 604 may be shaped as a cone that has an opening angle of between 0 and 90 degrees, such as between about 15 and about 75 degrees.

As used herein, including in the claims, the "distal" end of the implant is the end that is inserted first into a bone, such as an alveolar ridge, and is sometimes referred to in the art as the apical end, and the "proximal" end of the implant is the end of the implant opposite the distal end, e.g., that faces the oral cavity, and is sometimes referred to in the art as the coronal end. Similarly, "distal" means situated toward the distal end of the implant, and "proximal" means situated toward the proximal end of the implant.

The scope of the present invention includes embodiments described in the following patent applications, which are assigned to the assignee of the present application and are incorporated herein by reference. In an embodiment, techniques and apparatus described in one or more of the following applications are combined with techniques and apparatus described herein:

U.S. application Ser. No. 12/240,353, filed Sep. 29, 2008, which issued as U.S. Pat. No. 7,934,929;

U.S. application Ser. No. 12/485,199, filed Jun. 16, 2009, which issued as U.S. Pat. No. 8,029,284;

International Application PCT/IL2009/000931, filed Sep. 29, 2009, which published as PCT Publication WO 2010/035270;

International Application PCT/IL2010/000252, filed Mar. 24, 2010, which published as PCT Publication WO 2010/146573; and/or U.S. application Ser. No. 12/661,795, filed Mar. 24, 2010, which published as US Patent Application Publication 2010/0255446.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
advancing a drill having a distal end through an occlusal cortex into trabecular bone of an alveolar ridge; and
ceasing the advancing of the drill when the distal end of the drill reaches an occlusal surface of a superior cortex of the alveolar ridge, wherein the drill is a first drill, and further comprising, after ceasing the advancing, cutting into the superior cortex using a distal cutting surface of a cortex drill separate from the first drill, which cortex drill is shaped so as to define a shaft and a cutting protrusion that (a) is coaxial with the shaft and (b) defines at least the distal cutting surface.

2. The method according to claim 1, wherein the drill has a flat distal cutting edge, and wherein advancing and ceasing advancing comprise advancing and ceasing advancing the drill having the flat distal cutting edge.

3. The method according to claim 1, wherein ceasing the advancing comprises ceasing the advancing upon detecting a change in resistance when a distal end of the drill comes in contact with the occlusal surface of the superior cortex.

4. The method according to claim 3, wherein detecting the change in resistance comprises manually feeling the change in resistance.

5. The method according to claim 3, wherein detecting the change in resistance comprises using a tool to measure torque.

6. The method according to claim 1, wherein cutting into the superior cortex comprises cutting into the superior cortex using the distal cutting surface of the cortex drill in which the cutting protrusion has a diameter less than that of a portion of the shaft that is proximally adjacent the distal cutting surface, such that the cutting protrusion extends distally from the portion of the shaft at an interface that defines a shoulder, wherein the shoulder does not define a cutting surface.

7. The method according to claim 6, further comprising ceasing cutting into the superior cortex when the shoulder reaches the occlusal surface of the superior cortex.

8. The method according to claim 6, further comprising slowing advancing of the cortex drill into the superior cortex when the shoulder reaches the occlusal surface of the superior cortex.

9. The method according to claim 8, wherein cutting into the superior cortex using the distal cutting surface of the cortex drill comprises gauging a depth of penetration of the cortex drill into the superior cortex using visually-sensible fiducial designators distributed along the shaft of the cortex drill.

10. The method according to claim 1, wherein the distal cutting surface is an abrasive surface, and wherein cutting into the superior cortex using the distal cutting surface of the cortex drill comprises abrading the occlusal surface of the superior cortex using the distal cutting surface.

11. The method according to claim 1, further comprising, after cutting into the superior cortex using the distal cutting surface of the cortex drill:
withdrawing the cortex drill from the alveolar ridge; and
after withdrawing the cortex drill, cutting through the superior cortex using a dental implement other than the first drill and the cortex drill.

12. The method according to claim 11, wherein the dental implement is a dental implant, and wherein cutting through the superior cortex using the dental implement comprises cutting through the superior cortex using the dental implant.

13. The method according to claim 11, wherein the dental implement is a dental osteotome, and wherein cutting through the superior cortex using the dental implement comprises cutting through the superior cortex using the dental osteotome.

* * * * *